United States Patent

Collins et al.

[11] Patent Number: 5,853,428
[45] Date of Patent: Dec. 29, 1998

[54] METAL LIGAND CONTAINING BLEACHING COMPOSITIONS

[75] Inventors: Terrence J. Collins; Colin P. Horwitz, both of Pittsburgh, Pa.

[73] Assignee: Carnegie Mellon University, Pittsburgh, Pa.

[21] Appl. No.: 804,776

[22] Filed: Feb. 24, 1997

Related U.S. Application Data

[63] Continuation-in-part of Ser. No. 684,670, Jul. 22, 1996.
[51] Int. Cl.$^6$ .............................. D06L 3/00; D06L 3/06; D21C 9/16; D21C 9/12
[52] U.S. Cl. .................................. 8/107; 8/108.1; 8/111; 252/186.33; 510/311; 162/74; 162/78; 162/79
[58] Field of Search .................................. 540/460, 452, 540/465; 252/186.33, 186.43; 510/311; 162/4, 5, 6, 78, 79, 70, 74; 8/111, 107, 108.1

[56] References Cited

U.S. PATENT DOCUMENTS

| | | | |
|---|---|---|---|
| 3,736,224 | 5/1973 | Grayson et al. | 162/65 |
| 4,577,042 | 3/1986 | Collins et al. | 564/158 |

(List continued on next page.)

FOREIGN PATENT DOCUMENTS

95/24267  9/1995  WIPO .

OTHER PUBLICATIONS

Terrence J. Collins, Designing Ligands for Oxidizing Complexes, Dept. of Chem. Carnegie Mellon University, Accounts of Chemical Research, (1994) 27, p. 279.

(List continued on next page.)

*Primary Examiner*—Joseph D. Anthony
*Attorney, Agent, or Firm*—Kirkpatrick & Lockhart LLP

[57] ABSTRACT

The invention provides a novel composition for bleaching cellulose based materials, such as wood pulp and paper comprising:
(a) an oxidatively stable bleach activator having the structure

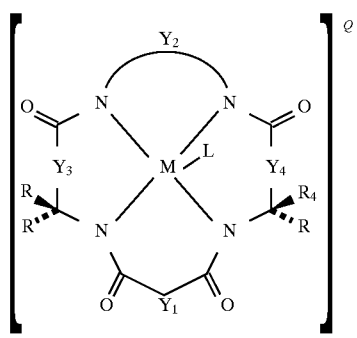

wherein $Y_1$, $Y_3$ and $Y_4$ each represents a bridging group, i.e., zero, one, two or three carbon containing nodes for substitution, while $Y_2$ is a bridging group of at least one carbon containing node for substitution, each said node containing a C(R), C($R_1$) ($R_2$), or a C(R)$_2$ unit and each R substituent is the same or different from the remaining R substituents and is selected from the group consisting of H, alkyl, cycloalkyl, cycloalkenyl, alkenyl, aryl, alkynyl, alkylaryl, halogen, alkoxy, phenoxy, CH$_2$CF$_3$, CF$_3$ and combinations thereof, or form a substituted or unsubstituted benzene ring of which two carbon atoms in the ring form notes in the Y unit, or together with a paired R substituent bound to the same carbon atom form a cycloalkyl or cycloalkenyl ring, which may include an atom other than carbon, e.g., cyclopentyl or cyclohexyl; M is a transition metal with oxidation states of I, II, III, IV, V, VI, VII or VIII or selected from Groups 3, 4, 5, 6, 7, 8, 9, 10, and 11 of the Periodic Table; Q is any counterion which would balance the charge of the compound on a stoichiometric basis; L is any labile ligand; and
(b) an effective amount of a source of an oxidant.

39 Claims, 5 Drawing Sheets

5,853,428
Page 2

U.S. PATENT DOCUMENTS

| | | | |
|---|---|---|---|
| 4,758,682 | 7/1988 | Collins et al. | 556/137 |
| 4,773,966 | 9/1988 | Huynh | 162/78 |
| 4,900,871 | 2/1990 | Ellis, Jr. et al. | 568/399 |
| 5,244,594 | 9/1993 | Favre et al. | 252/186.33 |
| 5,246,621 | 9/1993 | Favre et al. | 252/186.33 |
| 5,314,635 | 5/1994 | Hage et al. | 252/186.33 |
| 5,580,485 | 12/1996 | Feringa et al. | 510/311 |

OTHER PUBLICATIONS

Erich Stuart Uffelman, Macrocyclic Tetraamido–N–Ligands that Stabilize High Valent Complexes of Chromium, Maganese, Iron, Cobalt, Nickel, and Copper, California Institute of Technology, Aug. 19, 1991.

Kimberely K. Kostka, Synthesis and Characterization of High–Valent Iron Complexes of Macrocyclic Tetraamido–N–Ligands, Carnegie Mellon University, (Jul. 19, 1993).

Frank Runge et al, "Binding Equilibria of Multiazo Dyes with Polymeric Dye Transfer Inhibitors". (1996).

A. Paul Krapcho, Edwin G. E. Jahngen, Jr., and David S. Kashdan, Route to Monoesters of Malonic Acids, Tetrahedron Letters Nos. 32, pp. 2721–2723, (1994).

G. A. Fletcher and J. H. Jones, A List of Amino–Acid Derivatives Which Are Useful in Peptide Synthesis, Int. J. Peptide Protein Res. 4, 1972, 347–371, (Jun. 10, 1972).

Jose M. Workman, Routes to Multimetallic High Oxidation State Transition Metal Complexes, Carnegie Mellon University, Mellon College of Science, (Jul. 23, 1992).

Terrence J. Collins, Designing Ligands for Oxidizing Complexes, Department of Chemistry, Carnegie Mellon University, Accounts of Chemical Research, (1994) 27, p. 279.

Masaru Nakamura, Mitsuko Toda and Hiroko Saito, Fluorimetric Determination of Aromatuc Aldehydes With 4,5–Dimethoxyl–1,2–Diaminobenzene, Analytica Chimica Acta, 134 (1982) 39–45.

Erich Stuart Uffelman, Macrocyclic Tetraamido–N Ligands that Stabilize High Valent Complexes of Chrominum, Maganese, Iron, Cobalt, Nickel and Copper, California Institute of Technology, (Aug. 19, 1991).

Thoedora W. Greene, Protective Groups in Organic Synthesis, Harvard University, John Wiley & Sons, (1981).

Nathan L. Drake, Harry D. Anspon, et al. Synthetic Antimarlarials. Some Derivatives of 8–Aminoquinoline, Laboratories of the University of Maryland, vol. 68, p. 1536, Aug. 1946.

Richard J. Bushby and Michael D. Pollard, The Introduction of Alkylidene Substituents into the 4–Position of the 3,3,5, 5,–Tetramethyl—pyrazoline Nucleus by the Thioketone plus Diazoalkane Reaction: Synthesis of Tetrasubstituted Episulphides and Alkenes. (Nov. 15, 1978).

Select Pages from an Introductory to Pulp Bleaching, TAPPI Press (1986).

Kimberly L. Kostka, Brian G. Fox, High–Valent Transition metal Chemistry. Mossbauer and EPR Studies of High–Spin (S=2) Iron (IV) and Intermediate–Spin (S=3/2) Iron(III) Complexes with a Macrocyclic Terraamido–N Ligand. (Jan. 4, 1993).

Mohammad Shakir and Saji P. Varkey, A New Synthetic Route for the Preparation of a New Series of 14–22–Membered Tetraoxomacrocyclic Tetraamines and Their Transition Metal Complexes. (Jul. 12, 1994).

Reaction conditions:

Catalyst: [Fe(DCB*) (H₂O)]⁻
Oxidant: 5000 equiv. H₂O₂
T: 25° C
pH: 10(0.1 M Na₂CO₃/NaHCO₃)
Sequesterant: Dequest 2066

✶ = add 60 μL of saturated solution of alkali lignin and H₂O₂ (5000 equiv)

Catalyst:
0.4 mM [Fe(H2O)DCB*]⁻
0.4 mM [Fe(H2O)DCB]⁻
0.0 mM catalyst
12 μM pinacyanol chloride dye
4 mM 30% H2O2 oxidant
pH ~ 9 NaHCO3/Na2CO3

* = dye addition     time / s

METAL LIGAND CONTAINING BLEACHING COMPOSITIONS

This application is a continuation-in-part of co-pending U.S. application Ser. No. 08/684,670, filed Jul. 22, 1996 allowed.

This work was supported by the National Science Foundation, grant CHE9319505, and the National Institute of Health, grant GM-44867.

BACKGROUND OF THE INVENTION

1. Field of the Invention

The invention relates to the use of macrocyclic metal ligand complexes as bleaching catalysts, and more particularly, to transition metal complexes of macrocyclic tetraamide ligands as catalysts for enhancing oxidative bleaching reactions.

2. Brief Description of the Background of the Invention

The United States and Canada are the world's leading producers of wood pulp used for the production of paper and paper board. In 1983, the United States produced over 41 million metric tons of pulp, 39% of the world capacity. The worldwide level of production has been increasing dramatically since then. Pulp, which is made either mechanically or chemically from wood, contains 1) cellulose, a linear polymer of d-glucose of the formula $-(C_6H_{10}O_5)-$; 2) lignin, an amorphous nonuniform three dimensional molecule having the following general composition, $C_9H_{8.83}$ $O_{2.37}$ $(OCH_3)_{0.96}$; and 3) extractives, components of the wood pulp which are typically extracted prior to use of the pulp in a paper making process. See generally, W. G. Glasser and S. Sarkanen, eds. "LIGNIN PROPERTIES AND MATERIALS," American Chemical Society Symposium, Series 397.

Desirable qualities for paper include strength, whiteness and brightness. The strength of the paper is related to the viscosity of the pulp employed in its manufacture which, in turn, is related to the condition of the cellulose after the pulping operation. Molecular cellulose, as explained above, is a linear chain of d-glucose which naturally forms long fibers. The longer the individual cellulose fibers, the higher the viscosity of the pulp, and in turn, the greater the strength of the paper. Thus, during processing, it is most desirable to avoid cleaving the cellulose polymers into smaller units.

Whiteness is based on the appearance of the paper to observers and its measure is therefore subjective. Brightness is a measure of reflected light at 475 nm. The more incident light that is reflected, rather than absorbed, the brighter the paper.

Brightness is obtained by bleaching. Pulp bleaching is defined as the treatment of cellulose fibers with chemicals to increase brightness. Bleaching chemicals increase brightness by removing and decolorizing the lignin in the pulp. Lignin exhibits a yellowish to a deep brown color, depending on the type of wood.

The most common bleaching chemicals are the oxidants chlorine, hypochlorite and chlorine dioxide. Oxygen gas in conjunction with NaOH may also be used, but requires expensive equipment and must be used in large amounts. Oxygen also results in loss of pulp strength resulting from free radical damage to the cellulose polymers.

Chlorine and hypochlorite can result in loss of strength if used improperly, but in general are effective and easy to use oxidants. Chlorine dioxide achieves a high level of brightness without pulp degradation. However, the chlorine based oxidants all produce as effluent chlorinated byproducts that are hazardous to the environment and to health. In addition, chlorine, for example, can react violently with combustible materials. It reacts with $H_2S$, CO and $SO_2$ to form toxic and corrosive gases; and, in liquid form, causes burns, blistering and tissue destruction. In gaseous form, it causes severe irritation to eyes, nasal passages and respiratory tissue. In high doses, it can be lethal.

Chlorine dioxide bleach decomposes into $Cl_2$ which is toxic and corrosive.

Notwithstanding the hazards to the environment, the chlorine-based oxidants are the most widely used for pulp bleaching in the United States. Commercial pulp and paper bleaching facilities actually uses a combination of several methods. One widely used bleaching sequence begins with chlorination, followed by extraction with NaOH, treatment with chlorine dioxide, more NaOH extraction and then more chlorine dioxide treatment. A modification of that sequence adds a hypochlorite oxidation step between the first NaOH extraction and first treatment with chlorine dioxide. In another sequence, the second NaOH extraction and second chlorine dioxide treatment are eliminated.

An alternative to the chlorine based oxidants for bleaching is hydrogen peroxide. $H_2O_2$ oxidizes and brightens lignin and produces high yields of pulp. It is easy to use and does not require expensive equipment. In use, $H_2O_2$ dissociates to produce the perhydroxyl ion, OOH—, which decolorizes lignin and does not attack cellulose. However, if $H_2O_2$ decomposes, it produces free radicals of oxygen, $.O_2^-$, and hydroxide, .OH, which fragment the lignin and degrade the cellulose. While hydrogen peroxide itself is a strong oxidant which can burn skin and mucous membranes, it is not a serious hazard in low (<8%) concentrations and its use does not introduce elemental toxicity into the environment. The major drawback to use of $H_2O_2$ as the oxidant for pulp and paper bleaching is that it is very slow and expensive to use. Although $H_2O_2$ would clearly be preferred for its environmentally friendly characteristics, the slow bleaching rate and the high cost associated with its use contribute to reducing its commercial desirability. When used commercially, it is as an adjunct to chlorination and/or chlorine dioxide bleaching or to bleach the effluent.

Hydrogen peroxide, and other peroxy compounds which yield hydrogen peroxide in aqueous solution, have long been known for use in fabric and surface bleaching. However, peroxy compounds, such as sodium perborate (monohydrate or tetrahydrate), sodium percarbonate, and the like, have relatively mild bleaching performance at low temperatures (e.g., below 100° F./38.8° C.). Organic peroxyacids, such as perbenzoic acid, are stronger oxidants, but are often unstable unless stabilized by costly and cumbersome methods. In addition, the pre-made peroxyacids are often cost-ineffective to manufacture. Bleach activators, or peracid precursors, such as esters, ketones, nitriles, or the like, are often effective at enhancing the efficacy of peroxy compounds. However, the bleach activators must usually be present in stoichiometric or greater quantities and can also be costly to manufacture.

Transition metal chelates, especially those using manganese and iron, are known as bleaching catalysts for peroxy compounds. These are represented by, for example, Favre et al., U.S. Pat. No. 5,246,621, Bragg et al., U.S. Pat. No. 5,002,682, Postlethwaite, U.S. Pat. No. 4,119,557, and Ellis, Jr., et al., U.S. Pat. No. 4,900,871. These transition metal chelates can be used, for example, in laundering fabrics with an appropriate peroxy compound, for example, sodium perborate monohydrate.

While these transition metal chelates have been proven to improve the oxidizing power of peroxy compounds, they sometimes can mediate dye transfer and, even cause damage, to fabrics when used as bleaching activators.

Certain transition metal chelates have been researched for unrelated purposes. For example, complexes of high oxidation state transition metals are known to function as oxidants in numerous biological reactions under the influence of a protein matrix and in recent years a widespread interest in understanding the mechanism of action and the reactivity of certain monooxygenase catalysts has developed.

An exemplary program is described in Collins, T. J., "Designing Ligands for Oxidizing Complexes," *Accounts of Chemical Research,* 279, Vol. 27, No. 9 (1994). This article lays out a design oriented approach for obtaining ligands that are resistant to oxidative degradation when coordinated to highly oxidizing metal centers. Several diamido-N-diphenoxido and diamido-N-alkoxido acyclic chelate compounds and macrocyclic tetraamido-N chelate compounds are described in the Collins *Accounts of Chemical Research* article.

An azide based synthetic route to macrocyclic tetraamido ligands is described in Uffelman, E. S., Ph.D. Thesis, California Institute of Technology, (1992). Additionally, synthesis of an aryl bridged tetraamido ligand via the azide based route can proceed by using an aromatic diamine as a starting material.

However, the art has not recognized that certain macrocyclic tetraamido ligands will provide novel and unusually effective bleach activators for peroxy compounds. Additionally, it has not been taught, disclosed or suggested that these types of compounds will be unusually advantageous in the areas of pulp and paper bleaching.

SUMMARY OF THE INVENTION

The invention comprises a bleaching composition comprising:

(a) an oxidatively stable bleach activator having the structure

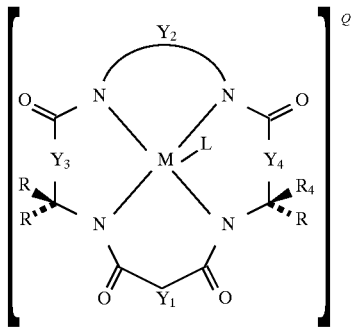

wherein $Y_1$, $Y_3$ and $Y_4$ each represents a bridging group, i.e., zero, one, two or three carbon containing nodes for substitution, while $Y_2$ is a bridging group of at least one carbon containing node for substitution, each said node containing a C(R), C($R_1$) ($R_2$), or a C(R)$_2$ unit and each R substituent is the same or different from the remaining R substituents and is selected from the group consisting of H, alkyl, cycloalkyl, cycloalkenyl, alkenyl, aryl, alkynyl, alkylaryl, halogen, alkoxy, or phenoxy, $CCH_2CF_3CF_3$ and combinations thereof, or form a substituted or unsubstituted benzene ring of which two carbon atoms in the ring form notes in the Y unit, or together with a paired R substituent bound to the same carbon atom form a cycloalkyl ring, which may include an atom other than carbon, e.g., cyclopentyl or a cyclohexyl ring; M is a transition metal with oxidation states of I, II, III, IV, V, VI, VII or VIII or selected from Groups 3, 4, 5, 6, 7, 8, 9, 10 and 11 of Periodic Table; Q is any counterion which would balance the charge of the compound on a stoichiometric basis; L is any labile ligand; and (b) an effective amount of a source of an oxidant.

Sequesterants, stabilizers and other standard pulp and paper bleaching adjuncts well known to those skilled in the art of pulp and paper bleaching may be added.

The preferred bleach activators are macrocyclic tetraamido compounds. Of these, those having a substituted aromatic substituent fused directly into the ligand's cyclic structure are especially preferred.

For example, a preferred compound has the structure:

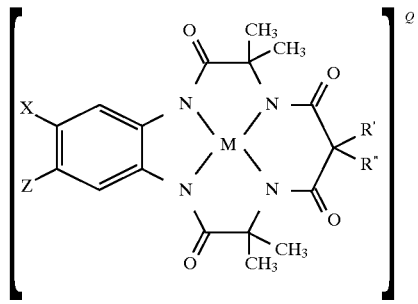

wherein X and Z may be H, electron donating or electron-withdrawing groups and R' and R" may be any combination of H, alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon; M is a transition metal with oxidation states of I, II, III, IV, V, VI, VII or VIII or selected from Groups 3, 4, 5, 6, 7, 8, 9, 10 and 11 of the Periodic Table; Q is any counterion which would balance the charge of the compound on a stoichiometric basis.

The rapid growth in the pulp and paper industry and the increasing reliance on chemical bleaching processes to provide bright, strong paper products necessarily increases the release of chlorinated byproducts into the environment. The industry needs a safer alternative to chlorine based oxidants for bleaching. Thus, there is a need for a method for bleaching pulp which significantly reduces the discharge of toxic substances into the environment. There is a further need for an environmentally nontoxic method which is easy to use and which will produce bright, strong paper.

The catalyst activator of the present invention has been determined to be particularly well-suited to handle this task. The activator has been shown to rapidly increase the rate of alkali lignin bleaching upon the addition of hydrogen peroxide. Furthermore, the activator of the present invention has been shown to be very stable.

It is therefore an object of this invention to provide a macrocyclic tetraamido compound as a bleach activator.

It is a further object of this invention to provide a novel bleach activator which has sustained catalytic stability in a buffered solution.

It is still a further object of this invention to provide a novel bleach activator which can be used in substoichiometric amounts relative to the oxidant compound.

The present invention provides a method of bleaching pulp, paper and other cellulose-based materials comprising generally, the steps of contacting such materials, in stream or batch form, with a source of an oxidant, preferably a peroxy compound, and more preferably hydrogen peroxide and/or its dissociation products, and catalytic, or substoichiometric, amounts of the bleaching activator of the composition described above. The method preferably further includes the addition of a sequesterant for shielding the peroxy compound from exposure to trace amounts of metal which can decompose it unnecessarily.

The method may be run at a variety of temperatures, but preferably within the range of ambient to 80° C., and more preferably between ambient to 40° C. Temperature, however, does not appear to be critical. A wide range of temperatures are suitable.

The preferred pH range is between 7 and 11, and preferably between 9 and 11.

While the activator of the present invention has been shown in other applications to be an excellent activator of oxidation reactions in solution in general, and particularly as an activator for activating strong O-atom transfer oxidants, such as hydrogen peroxide, t-butyl hydroperoxide, cumyl hydroperoxide, hypochlorite and peracids, the preferred use in the method of the present invention is as an activator of peroxy compounds, and most preferably as an activator of hydrogen peroxide in pulp and paper bleaching. The composition of the present invention enhances the oxidative capabilities of hydrogen peroxide thereby greatly enhancing the commercial utility of this environmentally friendly oxidant.

The benefits to the environment can not be overstated. Thousands upon thousands of metric tons of environmentally undesirable and even highly toxic, mutagenic or carcinogenic byproducts no longer need to be generated. The method of the present invention can significantly reduce, if not replace the use of chlorine-based bleaching oxidants and the toxic byproducts their use generates.

DETAILED DESCRIPTION OF THE PREFERRED EMBODIMENTS

Figure 1:
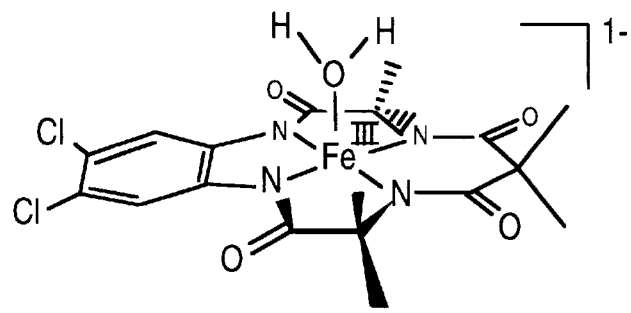
FIG. 1 is a graph showing the sustained activating stability of the preferred compound of the present invention when added with hydrogen peroxide to a sample of lignin as compared to a control using hydrogen peroxide alone.
Figure 1:
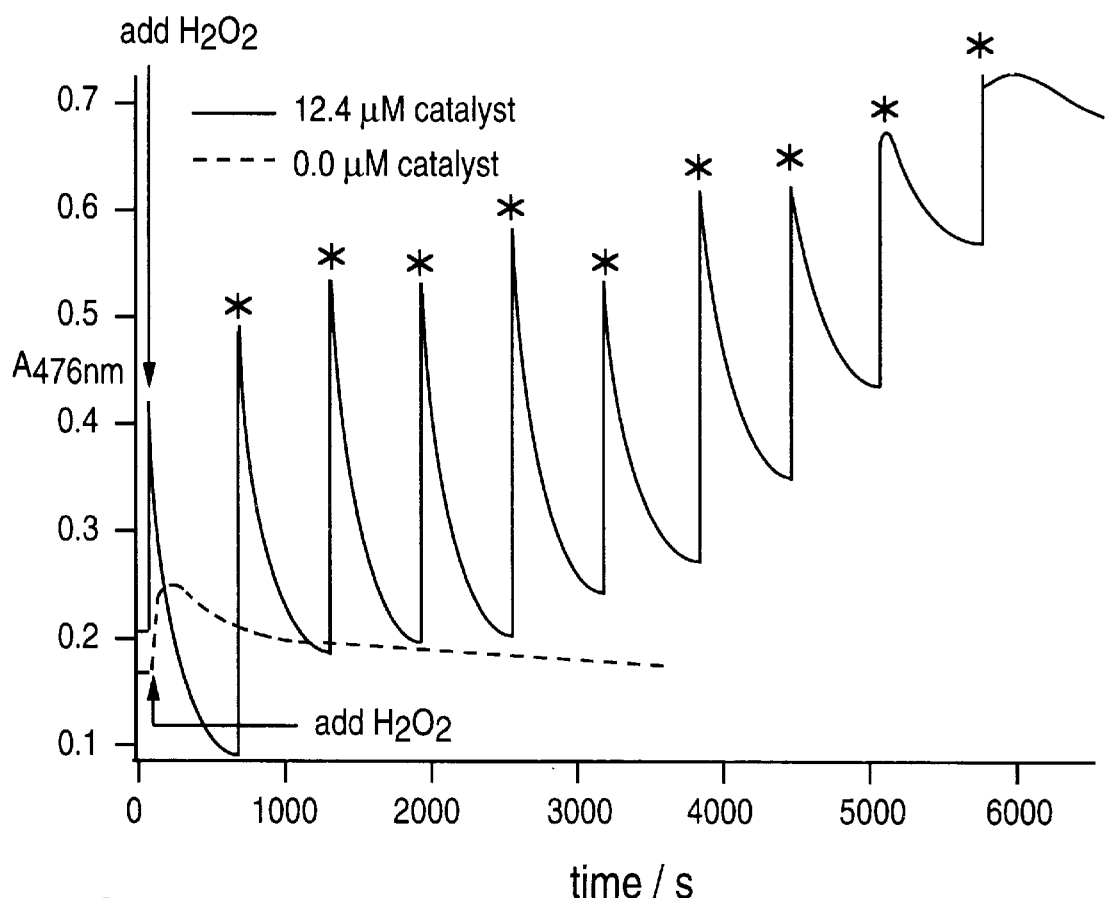
Figure 2:
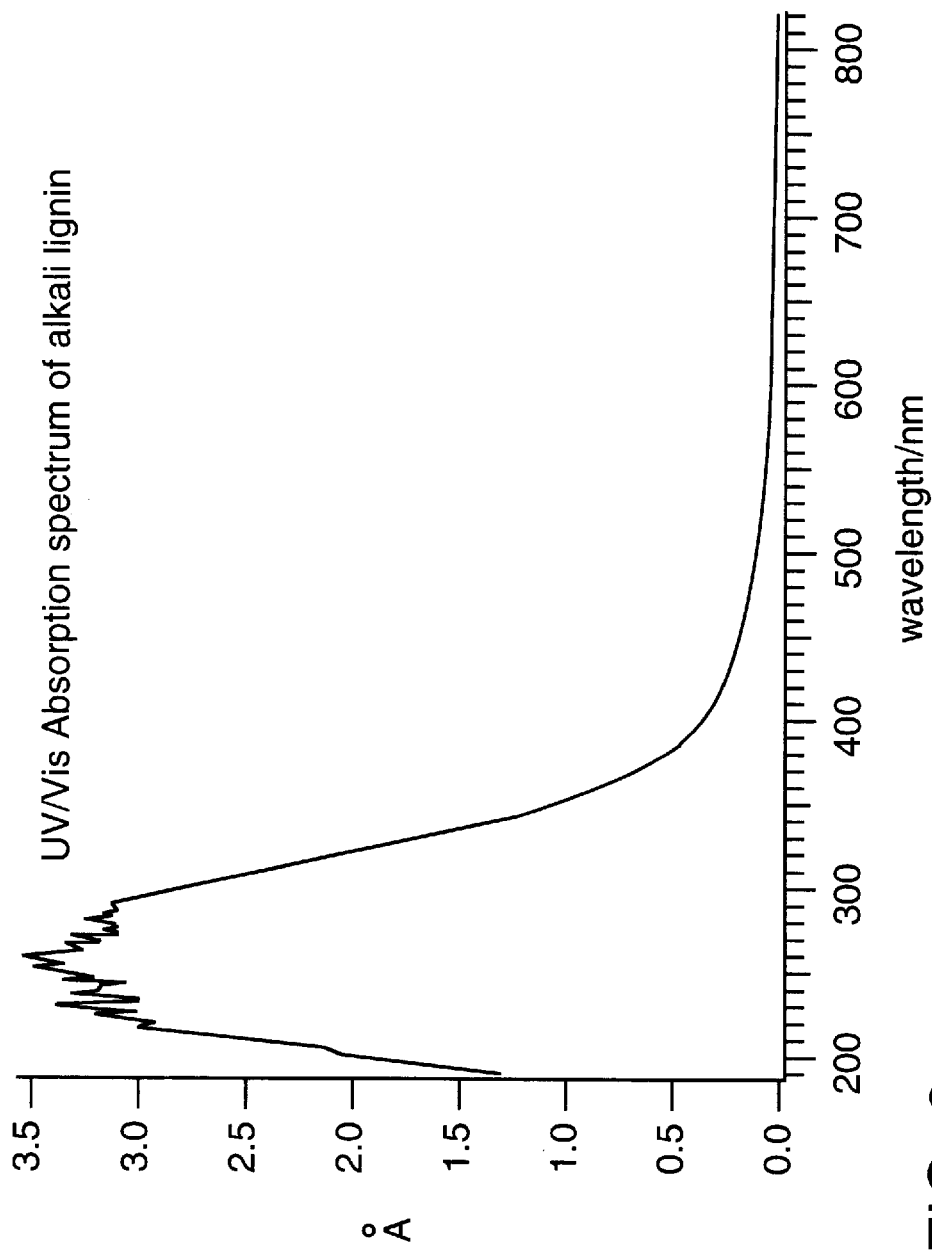
FIG. 2 represents the UV/Visual absorption spectrum of alkali lignin.
Figure 3:
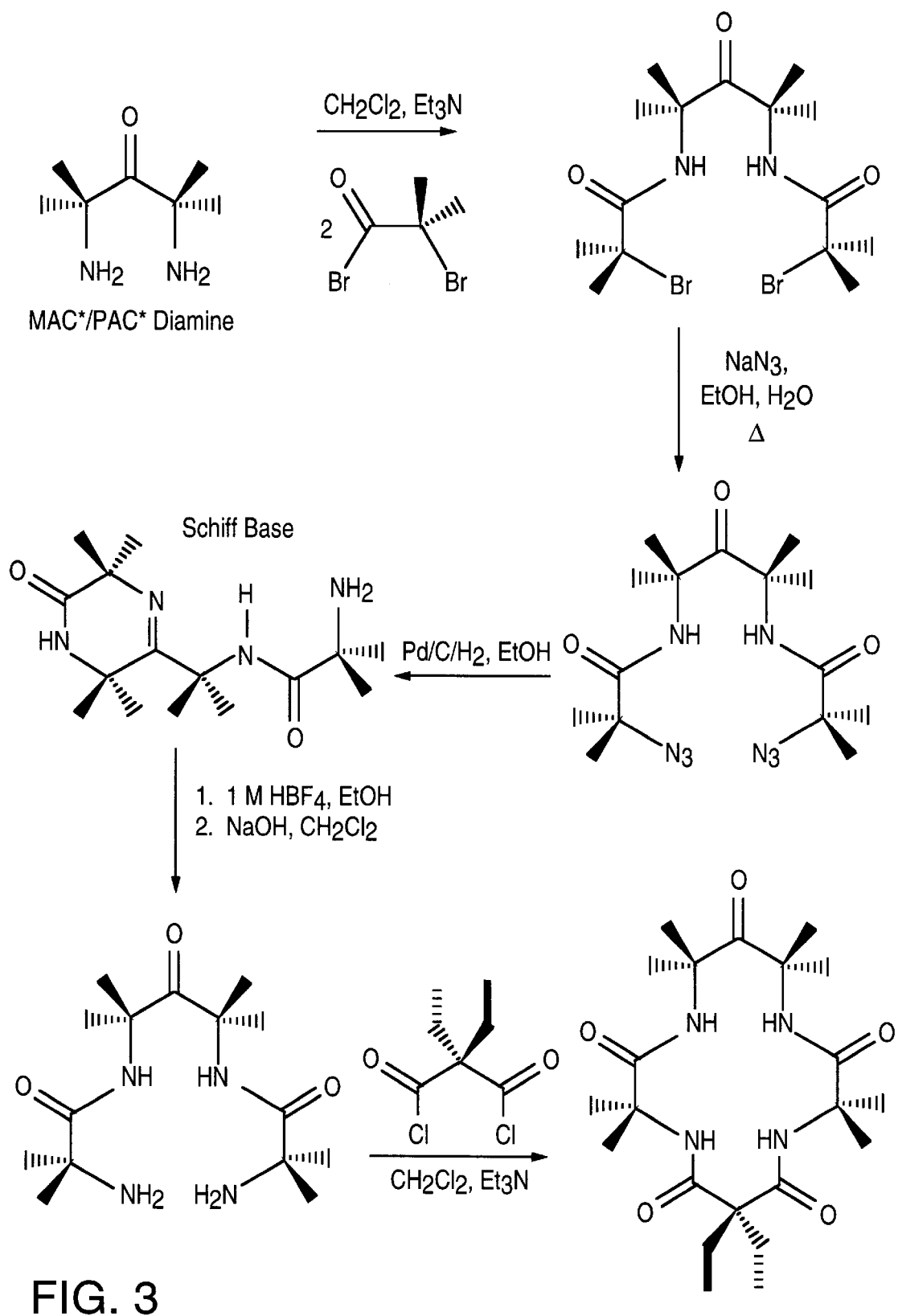
FIG. 3 depicts a synthetic route for preparing the macrocyclic tetraamido ligands of the invention via the azide route.
Figure 4:
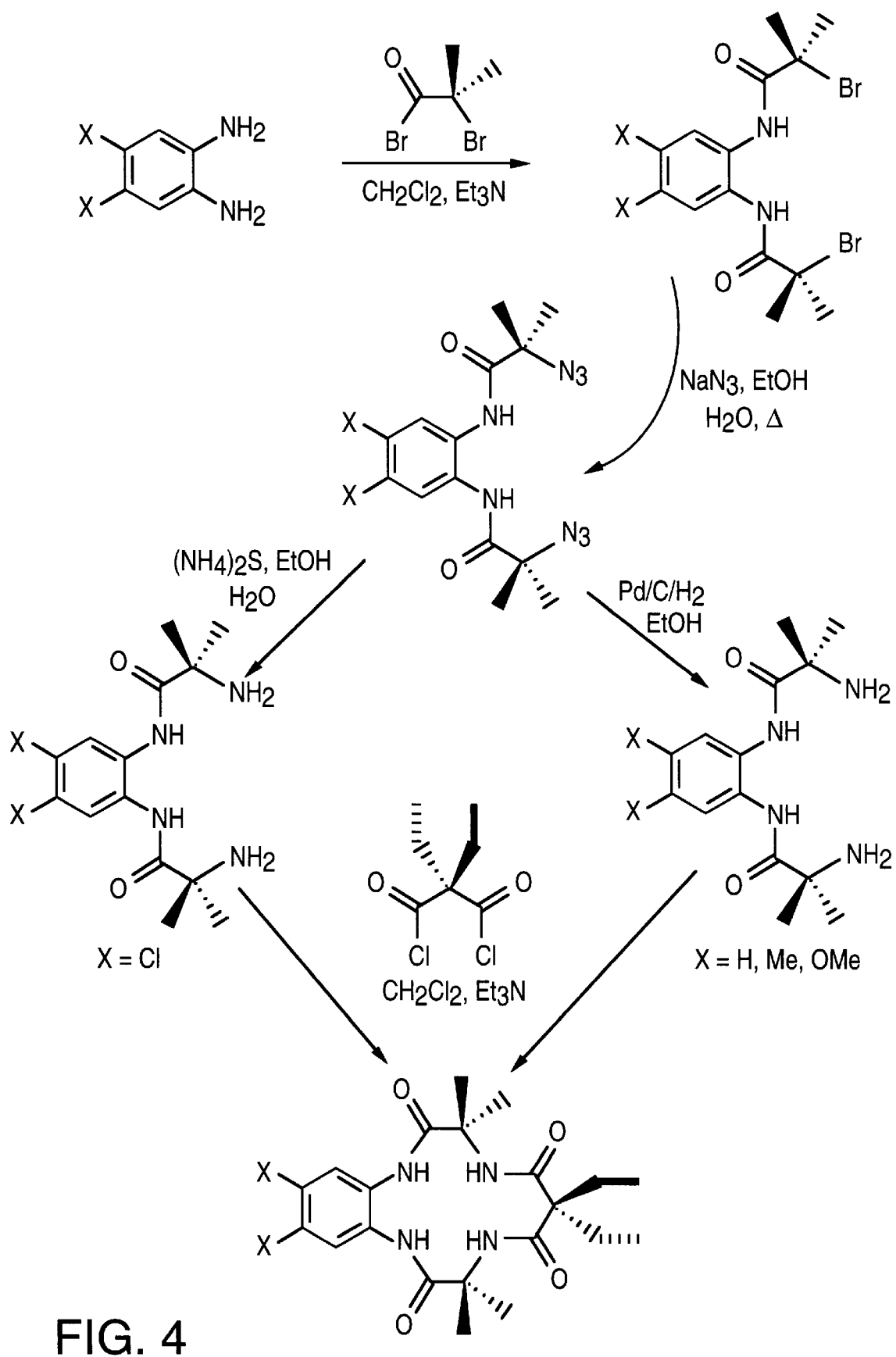
FIG. 4 depicts a synthetic route for preparing the macrocyclic tetraamido ligands of the invention via the azide route using an aromatic diamine as a starting material.

The invention comprises a bleaching composition comprising:

(a) an oxidatively stable bleach activator having the structure

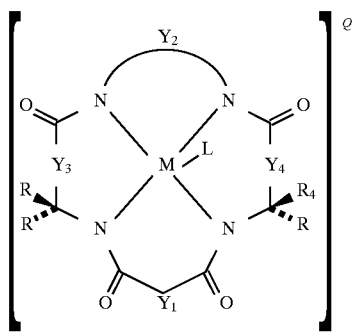

wherein $Y_1$, $Y_3$ and $Y_4$ each represents a bridging group, i.e., zero, one, two or three carbon containing nodes for substitution, while $Y_2$ is a bridging group of at least one carbon containing node for substitution, each said node containing a C(R), C($R_1$) ($R_2$), or a C(R)$_2$ unit and each R substituent is the same or different from the remaining R substituents and is selected from the group consisting of H, alkyl, cycloalkyl, cycloalkenyl, alkenyl, aryl, alkynyl, alkylaryl, halogen, alkoxy, or phenoxy, $CH_2CF_3CF_3$ and combinations thereof, or form a substituted or unsubstituted benzene ring of which two carbon atoms in the ring form notes in the Y unit, or together with a paired R substituent bound to the same carbon atom form a cycloalkyl or cycloalkenyl ring, which may include an atom other than carbon, e.g., cyclopentyl or a cyclohexyl ring; M is a transition metal with oxidation states of I, II, III, IV, V, VI, VII or VIII or selected from Groups 3, 4, 5, 6, 7, 8, 9, 10 and 11 of the Periodic Table; Q is any counterion which would balance the charge of the compound on a stoichiometric basis; L is any labile ligand; and (b) an effective amount of a source of an oxidant.

Of these, the preferred inventive macrocyclic tetraamido ligands have proven to be surprisingly effective in a diverse group of performance characteristics for bleach activators.

These ligands are prepared in accordance with the procedures set forth in the co-pending patent application of Gordon-Wylie et al., entitled SYNTHESIS OF MACROCYCLIC TETRAAMIDO-N LIGANDS, Ser. No. 08/681,187, filed Jul. 22, 1996, and include the preferred embodiments of the ligands set forth in detail in co-pending patent application of Collins et al., entitled LONG-LIVED HOMOGENOUS OXIDATION CATALYSTS, Ser. No. 08/681,237, filed Jul. 22, 1996, both of which are incorporated herein by reference.

1. The Macrocyclic Tetraamido Ligands
The inventive compounds have the structure:

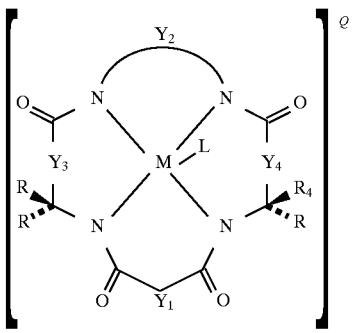

wherein $Y_1$, $Y_3$ and $Y_4$ each represents a bridging group, i.e., zero, one, two or three carbon containing nodes for substitution, while $Y_2$ is a bridging group of at least one carbon containing node for substitution, each said node containing node a C(R), C($R_1$) ($R_2$), or a C($R_2$) unit and each R substituent is the same or different from the remaining R substituents and is selected from the group consisting of H, alkyl, cycloalkyl, cycloalkenyl, alkenyl, aryl, alkynyl, alkylaryl, halogen, alkoxy, or phenoxy, $CH_2CF_3$, $CF_3$ and combinations thereof, or form a substituted or unsubstituted benzene ring of which two carbon atoms in the ring form nodes in the Y unit, or together with a paired R substituent bound to the same carbon atom form a cycloalkyl or cycloalkenyl ring, which may include an atom other than carbon, e.g., cyclopentyl or cyclohexyl ring; M is a transition metal with oxidation states of I, II, III, IV, V, VI, VII or VIII or selected from Group 3, 4, 5, 6, 7, 8, 9, 10 and 11 of the Periodic Table; Q is any counterion which would balance the charge of the compound on a stoichiometric basis; L is any labile ligand.

An especially preferred embodiment of these inventive compounds is represented by the structure of the macrocyclic tetraamido compounds:

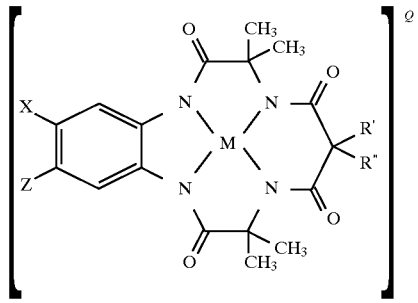

wherein X and Z may be H, electron donating or electron-withdrawing groups and R' and R" may be any combination of H, alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon: M is a transition metal with oxidation states of I, II, III, IV, V, VI, VII or VIII or selected from Groups 3, 4, 5, 6, 7, 8, 9, 10 and 11 of the Periodic Table; Q is any counterion which would balance the charge of the compound on a stoichiometric basis.

The X and Z groups can be H, or either electron donors or electron withdrawing groups. Electron withdrawing groups include halogens, such as Br, I and most preferably, $Cl^-$. Further, $SO^-_3$, $OSO^-_3$, $OSO_3R$ (R being defined, without limitation, as H, alkyl, aryl, alkylaryl) and $NO^-_2$ are appropriate groups. Electron donor groups include alkoxy (without limitation, methoxy, ethoxy, propoxy and butoxy), alkyl (without limitation, methyl, ethyl, propyl, n-butyl and t-butyl) and hydrogen. These groups change the electron density of the metal ligand complex and impact its reactivity.

R' and R" appear to have an impact on the sustained catalytic stability of the inventive macrocylic tetraamido ligands. Although each can be individually chosen from H, alkyl, alkenyl, aryl, alkynyl, halogen, alkoxy, or phenoxy substituents, short chain alkyl appears preferred. Especially preferred is when R' and R" are the same and are selected from ethyl and methyl, or when R' and R" combine to form a cycloalkyl or cycloalkenyl ring, especially cyclopentyl or cyclohexyl. The cycloalkyl ring may include at least one other atom other than carbon, such as, without limitation, N, O, or S. The most preferred and most robust embodiments are those in which R' and R" are the same and are selected from the group consisting of methyl, $CF_3$, hydrogen, halogen and a five membered ring formed together with the carbon atom to which both are bound. These latter groups are either unreactive, form strong bonds with the cyclic carbon, are sterically hindered, and/or are conformationally hindered such that intramolecular oxidative degradation is restricted.

The metal M is a transition metal with oxidation states of I, II, III, IV, V, VI, VII or VIII; or selected from Groups 3, 4, 5, 6, 7, 8, 9, 10 and 11 of the Periodic Table. It is preferably selected from the group consisting of Sc, Ti, V, Cr, Mn, Fe, Co, Ni, Cu, Zn, Mo and W.

Q is any counterion which would balance the charge of the compound on a stoichiometric basis. Both negative and positive counterions may be useful. A generally positively charged counterion is preferably chosen from, but not limited to: alkali metal counterions (e.g., K, Li, Na), $NR^*_4$ and $PR^*_4$, wherein each $R^*$ is individually selected from H, alkyl, aryl, alkylaryl, alkenyl, or can fuse together to form a cycloalkyl or cycloalkenyl or aryl ring which may contain at least one atom other than carbon. A generally negatively charged counterion is preferably chosen from, but not limited to $BF_4^{-1}$ and $PF_6^{-1}$.

L is any labile ligand which can attach to M. These include, preferably, but without limitations, $H_2O$, Cl, and C=N.

Because of the complex nature of these compounds, within the specification, they are not named, but for convenience are referred to by the substituents present in them. The structure represented above, for example, can be titled 5,6(4,5-Di-X-Benzo)-3,8,11,13-tetraoxo-2,2,9,9-tetramethyl-12,12-diethyl-1,4,7,10-tetraazacyclotridecane (or Tetramethyl diethyl di-X-benzene (TMDE-DXB, where X=Cl, H, Me, OMe)). Thus, for convenience, in the above structure, where there are two methyl groups each on the amine members of the ligand, and there are two ethyl groups acting as R' and R", the compound is referred to as TMDE. When R' and R" are methyl groups, the compound is referred to as TMDM. When the groups X and Z are both chloro, the compound is referred to as DCB. The preferred transition metal of the ligand is iron, so the compound can be referred to as Fe-DCB.

The conventional hydrogen peroxide bleaching methods are practiced at a pH within the range of 11 to 9 and at temperatures within the range of 30° to 80° C., and most often at 50° to 70° C. See, Charles, J. E. et al., 1980 TAPPI Pulping Conference Proceedings, TAPPI Press (1980). When the activator of the present invention is used, the temperature of the reaction can be reduced to ambient temperature. While the catalyst activator can be used at the higher conventional reaction temperatures, it also works well at 35° and 40° C. It is known that, for about every ten degrees in temperature, the reaction rate changes by a factor of about two. Thus, the reaction rate is much faster at higher temperatures. However, when bleaching pulp with the activator of the present invention, rates of $H_2O_2$ oxidation which are significantly better than those heretofore possible can be obtained with temperatures much lower than heretofore possible, thereby saving energy costs and increasing plant throughput rates. Preferred temperature ranges are therefore between ambient and 80° C., preferably between ambient and 70° C. and most preferably between ambient and 40° C. The bleaching system of the invention will even function effectively at sub-ambient temperatures. The wide range of temperatures over which the catalyst activator will function permits the method of the present invention to be used in existing facilities and in conjunction with other pulp and paper bleaching processes without having to make special temperature adjustments for the peroxide bleaching portion of a commercial production line, other than the advantageous change of lowering the temperature.

The pH of the oxidation reaction can also be lowered when using the activator of the present invention. Bleaching experiments run at pH 7 with $H_2O_2$ and the catalyst activator of the present invention bleached lignin at a rate believed to be an improvement over the conventional $H_2O_2$ bleaching rate, but not at the best rate possible for the activator. Far more rapid and satisfactory rates were obtained using the pH 10. Thus, the conventional pH range of 11 to 9 need not be altered by the addition of the catalyst activator of the invention, but can be if needed to avoid the decomposition of $H_2O_2$ that is known to occur at high pH. Decomposition can also be attributed to the presence of trace metals in the bleaching solution with the peroxy compound. Sequesterants and other known stabilizers are used to reduce the likelihood of decomposition due to the presence of trace metals. The experiments set forth below demonstrate that sequesterants may also be used with the catalyst activator of the present invention.

It is further believed that bleaching by the method of the present invention will produce very favorable kappa numbers, a measure used in the pulp and paper industry to show the amount of residual lignin following bleaching. The kappa number, which should be as low as possible, is a ratio of the difference between (1) the total oxidizing equivalent necessary for 100% lignin removal and (2) the difference between the actual oxidation achieved and the total oxidizing equivalent. It is obtained by testing with potassium permanganate according to procedures well known in the pulp and paper industry.

As the inventive macrocyclic tetraamido ligands are true catalysts, or catalyst activators, the amount thereof added to the bleaching compositions is generally substoichiometric. However, it is preferred, without limitation, to add about 0.0001 to about 999,999 parts per million (ppm), more preferably 0.001 to 100,000 ppm, to the compositions of the invention.

In the Experimental Section below, selected syntheses of the preferred macrocyclic tetraamido compounds are depicted. Additionally, tests were conducted to demonstrate the lignin bleaching capability and the dye transfer inhibition properties, the sustained catalytic activity and the stain removal performance of these inventive macrocyclic ligands.

2. Peroxy Compounds

The peroxy compound can be an organic or inorganic compound containing the —O—O-peroxide linkage. Exemplary compounds include hydrogen peroxide, hydrogen peroxide adducts, compounds capable of producing hydrogen peroxide in aqueous solution, organic peroxides, persulfates, perphosphates, and persilicates. Hydrogen peroxide adducts include alkali metal (e.g., sodium, lithium, potassium) carbonate peroxyhydrate and urea peroxide. Compounds capable of producing hydrogen peroxide in aqueous solution include alkali metal (sodium, potassium, lithium) perborate (mono-and tetrahydrate). The perborates are commercially available from such sources as Akzo N. V., and FMC Corporation. Alternatively, an alcohol oxidase enzyme and it appropriate alcohol substrate can be used as a hydrogen peroxide source. Organic peroxides include, without limitation, benzoyl and cumene hydroperoxides. Persulfates include potassium peroxymonosulfate (sold as Oxone®, E.I. duPont de Nemours) and Caro's acid.

An effective amount of peroxy compound is an amount sufficient to generate at least 0.001 ppm active oxygen (A.O.). While not limited thereto, it is preferred to produce from about 0.001 to about 1,000 ppm A.O. For fabric bleaching, from about 0.01 to about 50 ppm A.O. is preferred. A description of, and explanation of A.O. measurement is found in the article of Sheldon N. Lewis, "Peracid and Peroxide Oxidations, "In: *Oxidation,* 1969, pp. 213–258, which is incorporated herein by reference.

3. Cleaning and/or Laundering Adjuncts

The inventive macrocyclic tetraamido ligands can be combined with an oxidant bleach or detergent base, said base comprising: builders; and optionally, a surfactant selected from the group consisting of anionic, nonionic, cationic, amphoteric, zwitterionic surfactants, and mixtures thereof. Other adjunct materials may be present. These compounds can also be presented in a liquid base, for a hard surface, stain remover, or other surface cleaning/bleaching execution. These compounds may also be useful for pulp and textile bleaching processing. Each of these compounds, and adjunct materials suitable for use herein are further discussed below:

a. Builders

The builders are typically alkaline builders, i.e., those which in aqueous solution will attain a pH of 7–14, preferably 9–12. Examples of inorganic builders include the alkali metal and ammonium carbonates (including sesquicarbonates and bicarbonates), phosphates (including orthophosphates, tripolyphosphates and tetrapyrophosphates), aluminosilicates (both natural and synthetic zeolites), and mixtures thereof. Carbonates are especially desirable for use in this invention because of their high alkalinity and effectiveness in removing hardness ions which may be present in hard water, as well as their low cost. Carbonates can be used as the predominate builder. Silicates ($Na_2O:SiO_2$, modulus of 4:1 to 1:1, most preferably about 3:1 to 1:1) can also be used. Silicates, because of their solubility in water and ability to form a glassy matrix, can also be advantageously used as a binder for the detergent.

Organic builders are also suitable for use, and are selected from the group consisting of the alkali metal and ammonium sulfosuccinates, polyacrylates, polymaleates, copolymers of acrylic acid and maleic acid or maleic acid or maleic anhydride, citrates and mixtures thereof.

b. Fillers/Diluents

Fillers for the bleach composition or detergent are used to insure the correct amount or dose of washing or cleaning actives is delivered per wash or cleaning usage. Salts such as NaCl, NaCl, Na$_2$SO$_4$, and borax, are preferred. Organic diluents, such as sugar, are possible. If in a liquid execution, solvents (such as, without limitation, alkanols, gycols, glycol ethers, hydrocarbons, ketones, and carboxylic acids), liquid surfactants and water could be used as diluents.

c. Surfactants

Surfactants will generally be added to bleach or detergent formulations for removal of particular targeted soils, egs., nonionic surfactants on oily soils, and anionic surfactants on particulate soils. However, generally speaking, oxidant bleach compositions may contain little or even no surfactant.

Particularly effective surfactants appear to be anionic surfactants. Examples of such anionic surfactants may include the ammonium, substituted ammonium (e.g., mono-, di-, and tri-ethanolammonium), alkali metal and alkaline earth metal salts of C$_6$–C$_{20}$ fatty acids and rosin acids, linear and branched alkyl benzene sulfonates, alkyl sulfates, alkyl ether sulfates, alkane sulfonates, olefin sulfonates, hydroxyalkane sulfonates, fatty acid monoglyceride sulfates, alkyl glyceryl ether sulfates, acyl sarcosinates and acyl N-methyltaurides. Preferred are alkylaryl sulfonated surfactants, such as alkylbenezene sulfonates.

Other preferred surfactants of use include linear ethoxylated alcohols, such as those sold by Shell Chemical Company under the brand name NEODOL. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers of propylene oxide and ethylene oxide with propoxylated ethylene diamine. Also included are such semi-polar nonionic surfactants like amine oxides, phosphine oxides, sulfoxides, and their ethoxylated derivatives.

Suitable cationic surfactants may include the quaternary ammonium compounds in which typically one of the groups linked to the nitrogen atom is a C$_2$–C$_{18}$ alkyl group and the other three groups are short chained alkyl groups which may bear substituents such as phenyl groups.

Further, suitable amphoteric and zwitterionic surfactants which contain an anionic water-solubilizing group, a cationic group and a hydrophobic organic group may include amino carboxylic acids and their salts, amino dicarboxylic acids and their salts, alkylbetaines, alkyl aminopropylbetaines, sulfobetaines, alkyl imidazolinium derivatives, certain quaternary ammonium compounds, certain quaternary phosphonium compounds and certain tertiary sulfonium compounds. Other examples of potentially suitable zwitterionic surfactants can be found described in Jones, U.S. Pat. No. 4,005,029, at columns 11–15, which are incorporated herein by reference.

Further examples of anionic, nonionic, cationic and amphoteric surfactants which may be suitable for use in this invention are depicted in Kirk-Othmer, *Encyclopedia of Chemical Technology*, Third Edition, Volume 22, pages 347–387, and *McCutcheon's Detergents and Emulsifiers*, North American Edition, 1983, which are incorporated herein by reference.

As mentioned hereinabove, other common detergent adjuncts may be added if a bleach or detergent bleach product is desired. If, for example, a detergent composition is desired, the following ranges (weight %) appear practicable:

| | |
|---|---|
| 0.5–50.0% | Hydrogen Peroxide Source |
| 0.0001–10,000 ppm | Activator |
| 1.0–50.0% | Surfactant |
| 1.0–50.0% | Builder |
| 5.0–99.9% | Filler, stabilizers, dyes, fragrances, brighteners, etc. | d. Chelating Agents

In some of the compositions herein, it is especially preferred to include a chelating agent, most preferably, an aminopolyphosphonate. These chelating agents assist in maintaining the solution stability of the oxidant in order to achieve optimum performance. In this manner, they are acting to chelate free heavy metal ions. The chelating agent is selected from a number of known agents which are effective at chelating free heavy metal ions. The chelating agent should be resistant to hydrolysis and rapid oxidation by oxidants. Preferably, it should have an acid dissociation constant (pK$_a$) of 1–9, indicating that it dissociates at low pH's to enhance binding to metal cations. The most preferred chelating agent is an aminopolyphosphonate which is commercially available under the trademark DEQUEST, from Monsanto Company. Examples thereof are DEQUEST 2000, 2041, 2060 and 2066. (See also Bossu, U.S. Pat. No. 4,473,507, column 12, line 63 through column 13, line 22, incorporated herein by reference). A polyphosphonate, such as DEQUEST 2010, is also suitable for use. Other chelating agents, such as ethylenediaminetetraacetic acid (EDTA) and nitrilotriacetic acid (NTA) may also be suitable for use. Still other new, preferred chelating agents are new propylenediaminetetraacetates, such as Hampshire 1,3 PDTA, from W. R. Grace, and Chel DTPA 100#F, from Ciba-Geigy A. G. Mixtures of the foregoing may be suitable. Effective amounts of the chelating agent range from 1–1, 000, more preferably 5–500, most preferably 10–100 ppm chelating agent in the wash liquor.

e. Other Adjuncts:

The standard detergent or oxidant bleach adjuncts can be included in the present invention.

These include enzymes are especially desirable adjunct materials in these detergent or oxidant bleach products. However, it may be preferred to include an enzyme stabilizer.

Proteases are one especially preferred class of enzymes. They are selected from acidic, neutral and alkaline proteases. The terms "acidic," "neutral," and "alkaline," refer to the pH at which the enzymes' activity are optimal. Examples of neutral proteases include MILEZYME (available from Miles Laboratory) and trypsin, a naturally occurring protease. Alkaline proteases are available from a wide variety of sources, and are typically produced from various microorganisms (e.g., *Bacillis subtilis*). Typical examples of alkaline proteases include MAXATASE and MAXACAL from International BioSynthetics, ALCALASE, SAVINASE and ESPERASE, all available from Novo Industri A/S. See also Stanislowski et al., U.S. Pat. No. 4,511,490, incorporated herein by reference.

Further suitable enzymes are amylases, which are carbohydrate-hydrolyzing enzymes. It is also preferred to include mixtures of amylases and proteases. Suitable amylases include RAPIDASE, from Societe Rapidase, MILEZYME from Miles Laboratory, and MAXAMYL from International BioSynthetics.

Still other suitable enzymes are cellulases, such as those described in Tai, U.S. Pat. No. 4,479,881, Murata et al., U.S. Pat. No. 4,443,355, Barbesgaard et al., U.S. Pat. No. 4,435,307, and Ohya et al., U.S. Pat. No. 3,983,082, each of which are incorporated herein by reference.

Yet other suitable enzymes are lipases, such as those described in Silver, U.S. Pat. No. 3,950,277, and Thom et al., U.S. Pat. No. 4,707,291, both incorporated herein by reference.

Still further enzymes of interest herein are peroxidases, such as horseradish peroxidase, and those disclosed in International Patent Publication WO 93/24628, incorporated herein by reference.

The enzyme may be present in an amount of about 0–5%, more preferably about 0.01–3%, and most preferably about 0.1–2% by weight of the detergent/bleach/cleaner base. Mixtures of any of the foregoing hydrolases are desirable, especially protease/amylase blends.

Additionally, optional adjuncts include dyes, such as Monastral blue and anthraquionone dyes (such as those described in Zielske, U.S. Pat. No. 4,661,293, and U.S. Pat. No. 4,746,461).

Pigments, which are also suitable colorants, can be selected, without limitation, from titanium dioxide, ultramarine blue (see also, Chang et al., U.S. Pat. No. 4,708,816), and colored aluminosilicates.

Fluorescent whitening agents are still other desirable adjuncts. These include the stilbene, styrene, and naphthalene derivatives, which upon being impinged by ultraviolet light, emit or fluoresce light in the visible wavelength. These FWA's or brighteners are useful for improving the appearance of fabrics which have become dingy through repeated soilings and washings. Preferred FWA's are Tinopal 5BMX-C and Tinopal RBS, both from Ciba Geigy A. G., and Phorwite RKH, from Mobay Chemicals. Examples of suitable FWA's can be found in U.S. Pat. Nos. 1,298,577, 2,076,011, 2,026,054, 2,026,566, 1,393,042; and U.S. Pat. Nos. 3,951,960, 4,298,290, 3,993,659, 3,980,713 and 3,627,758, each of which are incorporated herein by reference.

Anti-redeposition agents, such as carboxymethylcellulose, are potentially desirable. Next, foam boosters, such as appropriate anionic surfactants, may be appropriate for inclusion herein. Also, in the case of excess foaming resulting from the use of certain surfactants, anti-foaming agents, such as alkylated polysiloxanes, e.g., dimethylpolysiloxane, would be desirable. Fragrances are also desirable adjuncts in these compositions.

Additional organic bleach activators can be added, including, but not limited to, esters (see Fong et al., U.S. Pat. No. 4,778,618 and Rowland et al., U.S. Pat. No. 5,182,045), ketones, imides (See Kaaret, U.S. Pat. No. 5,478,569) and nitrites, each of which are incorporated herein by reference.

The additives may be present in amounts ranging from 0–50%, more preferably 0–30%, and most preferably 0–10%. In certain cases, some of the individual adjuncts may overlap in other categories. However, the present invention contemplates each of the adjuncts as providing discrete performance benefits in their various categories.

EXPERIMENTAL SECTION

Syntheses of Oxidatively Robust Tetraamido Ligands

Materials. All solvents and reagents were reagent grade (Aldrich, Aldrich Sure-Seal, Fisher) and were used as received. Microanalyses were performed by Midwest Microlabs, Indianapolis, Ind.

Mass Spectrometry. Electrospray ionization mass spectra were acquired on a FINNIGAN-MAT SSQ700 (San Jose, Calif.) mass spectrometer fitted with an ANALYTICA OF BRANFORD electrospray interface. Electrospray voltages of 2400–3400 V were utilized. Samples were dissolved in either acetonitrile or dichloromethane at concentrations of approximately 10 pmol/$\mu$l and were introduced into the ESI interface prior to data acquisition by direct infusion at a flow rate of 1 l/min and were introduced prior to data acquisition. Positive ion electron impact ionization (70 ev) MS experiments were performed on a FINNIGAN-MAT 4615 quadrupole mass spectrometer in conjunction with an INCOS data system. The ion source temperature was 150° C. and the manifold chamber temperature was 100° C. Sample introduction was by means of a gas chromatograph or a direct insertion probe. Positive ion fast atom bombardment mass spectra were acquired on a FINNIGAN-MAT 212 magnetic sector instrument in combination with an INCOS data system. The accelerating voltage was 3 kV and the ion source temperature was approximately 70° C. An ION TECH saddle field fast atom gun was employed with xenon at 8 keV. Thioglycerol was utilized as the FAB matrix. Positive ion electron impact ionization (70 eV) MS/MS experiments were performed on a FINNIGAN-MAT TSQ/700 tandem quadrupole mass spectrometer. Sample introduction was by means of a direct insertion probe. The ion source was maintained at 150° C. and the manifold chamber was held at 70° C. Collision-induced dissociation (CID) was achieved by introducing argon into the center rf-only collision octapole until the pressure in the manifold reached 0.9–2.5×10$^{-6}$ Torr. The nominal ion kinetic energy for CID product ions was <35 eV (laboratory reference). High resolution data were obtained on a JEOL JMS AX-505H double focusing mass spectrometer in the EB configuration using a resolution of 7500. Sample introduction was by means of a gas chromatograph or direct insertion probe. During mass spectral acquisition, perfluorokerosene was introduced into the ion source by means of a heated inlet. Exact mass assignments were obtained by computer-assisted interpolation from the masses of perfluorokerosene. GC/MS conditions: column, 20 m×0.25 mm DB-1701 (J & W Scientific); carrier gas, helium with a linear velocity of 40 cm/sec; injector, 125° C.; column temperature, 35° C. for 3 min, followed by an increase at 10° C./min to 100° C.; injection, split mode, appx. 50:1 ratio.

Spectroscopic Methods. 300 MHz $^1$H NMR spectra and 75 MHz $^{13}$C NMR spectra were obtained on an IBM AF300 instrument using an OXFORD Superconducting magnet system, data acquisition was controlled by BRUKER software. Infrared spectra were obtained on a MATTSON GAL-AXY Series 5000 FTIR spectrometer controlled by a MACINTOSH II computer. UV/vis spectra were obtained on a HEWLETT PACKARD 8452A spectrophotometer driven by a ZENITH Z-425/SX computer. Conventional X-Band EPR spectra were recorded on a BRUKER ER300 spectrometer equipped with an OXFORD ESR-900 helium flow cryostat. Mossbauer spectra were obtained on constant acceleration instruments and isomeric shifts are reported relative to an iron metal standard at 298 K. In order to avoid orientation of polycrystalline samples by the applied magnetic field, the samples were suspended in frozen nujol.

Syntheses of Macrocyclic Tetraamido-N Donors Ligands

General Reaction Scheme

Depicted below is the preferred reaction sequence for synthesizing the inventive macrocyclic tetraamido ligands:

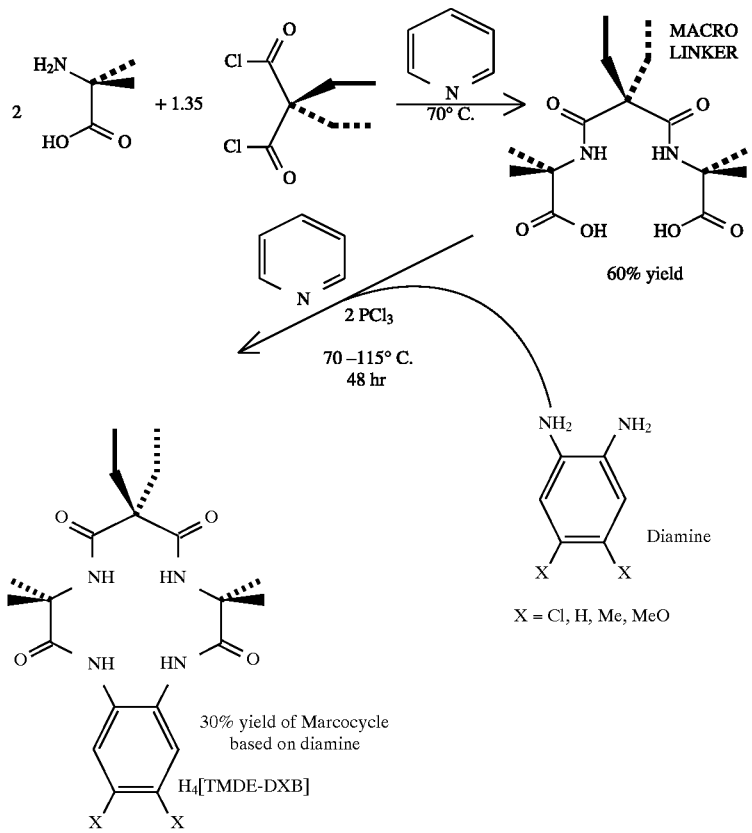

An α-amino carboxylic acid is mixed with an activated malonate in pyridine at temperatures less than 70° C. After the selective double coupling reaction is complete, 72–144 hrs., the MACRO LINKER (A—L—A) is isolated. In a second step, a diamine, preferably an o-phenylene diamine, is added to a pyridine solution of the MACRO LINKER in the presence of a coupling agent, preferably $PCl_3$ or pivaloyl chloride. The ring closure (a double coupling) reaction is allowed to proceed at reflux for 48–110 hrs., and then the desired macrocyclic tetraamide is isolated in good yield.

In the following Examples 1–25, various portions of the reaction steps are portrayed. Examples 26–39 demonstrate performance attributes and advantages of the invention for oxidation reactions involving lignin bleaching and dye bleaching.

EXAMPLE 1

Macro Linker Intermediate (A—L—A) synthesis, from α-methyl alanine and diethyl malonyl dichloride (a Tetramethyl Diethyl substituted intermediate).

A two-neck flask (1 L) fitted with a pressure equalizing addition funnel (250 mL) and a septum is placed under $N_2$ α-amino isobutyric acid (i.e. α-methyl alanine) (20.62 g, 0.2 mol) and dry pyridine (250 mL, dried over 4 Å mol sieves) are added to the flask and heated 60°–70° C. with stirring, then diethyl malonyl dichloride (23.23 mL, 0.135 mol) dissolved in dry pyridine (100 mL, dried over 4 Å mol sieves) is added to the addition funnel. The contents of the addition funnel are added (dropwise, 1 h) to the reaction and the acylation allowed to proceed (60°–70° C., 30–36 h) under $N_2$ or with a drying tube fitted. Once the acylation is complete the reaction is quenched by adding $H_2O$ (30 mL) and stirring (60°–70°C., 24 h). The solvent volume is reduced on the rotary evaporator to give an oil, then HCl (conc., ca. 25 mL) is added to a final pH of 2–3. The hot solution is set in the refrigerator (4° C., 15 h), and the resulting tan product collected by frit filtration, and washed thoroughly with acetonitrile (2×100 mL). The air-dried white product (16.5–19.8 g, 50–60% yield) should be stored in a dessicator. This product is usually pure enough for ring closure reactions, but recrystallization may occasionally be required. Characterization: $^1H$ NMR spectrum ($d^2$-pyridine) δ[ppm]: 8.9 (s, 2H, NH amide); 2.2 (q, 4H); 1.8 (s, 12H); 1.2 (t, 6H). IR(Nujol mull) : ν[$cm^{-1}$]=3310 (amide NH) ; 1721 (carboxylic CO) ; 1623 (amide CO). Anal. Calcd for $C_{15}H_{21}N_2O_6$; C, 54.53; H, 7.93; N, 8.48. Found: C, 54.48; H, 7.88; N, 8.47.

EXAMPLE 2

Large Scale, Macro Linker Intermediate (A—L—A) synthesis, from α-methyl alanine and diethyl malonyl dichloride (a TMDE substituted intermediate).

A two-neck flask (2 L, RB+Claisen) fitted with a pressure equalizing addition funnel (250 mL) and septa, is placed under $N_2$ α-aminoisobutyric acid (i.e. α-methyl alanine) (90.3 g, 0.9 mol) is added, anhydrous pyridine (1.4 L, sure seal) is cannulated into the flask and the reaction mix heated to 45°–55° C. and stirred. Pyridine (100 mL, sure seal) and then diethyl malonyl dichloride (104.4 mL, 0.61 mol) are cannulated into the addition funnel. The contents of the addition funnel are added (dropwise, 3–4 h) to the reaction, the addition funnel is then removed, and the acylation allowed to proceed (55°–65° C., 120–130 h) under $N_2$. Once the acylation is complete the reaction is quenched by adding $H_2O$ (100 mL) and stirring (60°–70° C., 24–36 h) The solvent volume is reduced on the rotary evaporator to give an oil, then HCl (conc., ca. 110 mL) is added to a final pH of 2–3. The hot solution is set in the refrigerator (4° C., 15 h), and the resulting tan product collected by frit filtration, and washed thoroughly with acetonitrile (700 mL, 150 mL) by stirring in an erlenmeyer flask. The air-dried white product (87.9 g, 60% yield), is crushed in a mortar and pestle and stored in a dessicator. The large scale reaction amide intermediate product is more likely to need recrystallization before use in ring closure reactions.

EXAMPLE 3

Recrystallization of the TMDE substituted intermediate

Crude TMDE intermediate from Example 2 (50.4 g., 0.153 mol) is dissolved in $H_2O$ (500 mL, deionized) by adding $Na_2CO_3$ (16.2 g, 0.153 mol) in three aliquots slowly and carefully to avoid excessive frothing, with good stirring and mild heating. The solution is brought to a boil, filtered and acidified with HCl (conc., 30 mL, 0.36 mol). The solution is allowed to cool (overnight, 4° C.) and the white precipitate filtered off and washing with acetonitrile (250 mL). The air dried product (38.8–45.4 g, recryst. yield 77–90%) should be stored in a dessicator.

EXAMPLE 4

Hexa Methyl (HM) Intermediate (A—L—A)

The synthesis of the HM intermediate is identical to that for the TMDE intermediate in Example 2 with the following exceptions, dimethyl malonyl dichloride (17.8 mL, 0.135 mol) is substituted for diethyl malonyl dichloride, and the reaction temperature must be decreased to 55°–65° C. due to the lower boiling point of the acylating agent. The yield of hexamethyl intermediate is 45–60%. Characterization: $^1$H NMR ($d^5$ pyridine, δ[ppm]); 9/2–9.8 br s, 2H (carboxylic OH), 8.23 s, 2H (amide), 1.87 s 12H ($CH_3$), 1.74 s 6H ($CH_3$). IR (nujol/NaCl) ν[cm$^1$]; 3317.0 (amide NH); 1717.9 (carboxylic CO); 1625.7 (amide CO). Anal. (dried at 100° C.) Calcd. for $C_{13}H_{22}N_2O_6$; C 51.63, H 7.34, N 9.27. Found; C 51.64, H 7.35, N 9.33.

EXAMPLE 5

Recrystallization of HM Intermediate

Crude hexamethyl (HM) intermediate was recrystallized in the same manner as the TMDE amide intermediate. Due to the slightly higher water solubility of the HM amide intermediate a little less $H_2O$ should be employed.

EXAMPLE 6

Di CyHex Di Ethyl Intermediate

A round bottom flask (500 mL), is charged with 1-amino-1-cyclohexane carboxylic acid (15 g, 0.1 mol), then fitted with a pressure equalizing addition funnel (40 mL), capped with a septum, and purged with nitrogen. Anhydrous pyridine (300 mL) is cannulated into the reaction flask through the addition funnel, and 20 mL into the addition funnel. Start heating the system and stabilize the temperature at 60° C. Once 60° C. is reached, one-third of the total diethyl malonyl dichloride to be utilized in the reaction (i.e. 6 mL, 0.033 mol) is added via syringe to the addition flask. The mixture of pyridine/diethyl malonyl dichloride is added dropwise to the reaction and the acylation allowed to proceed for 12 hours. A second (6 mL, 0.033 mol) and third aliquot (6 mL, 0.033 mol) are added at 12 hour intervals. After all of the acylating agent has been added and allowed to react (total reaction time 48–56 h), 20 mL of water is added dropwise to the reaction. The reaction is heated for an additional 24 hours to ring open the mono and bis oxazalone intermediates and yield the diamide dicarboxylic acid. Removal of the pyridine by rotary evaporation yields a pale yellowish tan sludge which is acidified to pH 2 with HCl(conc.). The crude product is collected by filtration, washed with acetonitrile and air dried to yield the white DiCyHexDE-amide intermediate (16 g, 74%). Characterization: $^1$H NMR ($d^5$-pyridine) δ[ppm]: 8.30 (s, 2H, NH amide), 2.60 (m, 4H, cyhex), 2.25 (q,4H, ethyl $CH_2$), 2.15 (m, 4H, cyhex), 1.8–1.5 (m, 10H, cyhex), 1.25 (m, 2H, cyhex), 1.20 (t, 6H, ethyl $CH_3$). $^{13}$C NMR broadband decoupled ($d^5$-pyridine) δ[ppm]: 178.0, (carboxylic CO), 174.3 (amide CO), 60.5 (cyhex quat), 59.4 (malonyl quat), 33.0 (cyhex α $CH_2$), 30.3 (ethyl $CH_2$) 26.0 (cyhex γ $CH_2$), 22.3 (cyhex β $CH_2$), 9.9 (ethyl $CH_3$). IR (nujol/NACl) ν[cm-$^1$]: 3307 (amide NH) ; 3150 (sh, br, m, amide NH/carboxylic OH), 3057 (s, str, H bonded amide NH/carboxylic OH), 1717 (s, str, carboxylic CO); 1621 (s, str, amide CO). Anal. Calcd for $C_{21}H_{34}N_2O_6$: C, 61.44; H, 8.35; N, 6.82. Found: C, 61.41; H, 8.38, N, 6.90%.

EXAMPLE 7

Di CyHex Diethyl Mono Oxazalone

Failure to quench the Di CyHex Di Ethyl Intermediate Reaction (with heat & water, see above) at a stoichiometry of 1.35 diethyl malonyl dichloride; 2 CY Hex amino acid, leads to a mixture of the DiCyHexDE-amide intermediate and mono oxazalone products. The DiCyHexDE Mono Oxazalone product is moderately soluble in boiling cyclohexane while the cyclohexyl amide intermediate is not, allowing for a simple separation of the product mixture, ca. 10 g of mixed amide intermediate and mono oxazalone containing some residual $CH_2Cl_2$ was boiled with vigorous stirring in 400–500 mL cyclohexane. The insoluble DiCyHexDE-amide intermediate product was collected by hot gravity filtration while the mono oxazalone product crystallized out gradually as the cyclohexane solution cooled and evaporated. Yield amide intermediate ca. 6 g, yield mono oxazalone ca. 4 g. Characterization of the mono oxazalone: $^1$H NMR ($d^5$-pyridine) δ[ppm]: 9.7 (s, 1H, amide NH), 2.7–1.6 (unresolved Cy Hex groups), 1.05 (t, 6H, ethyl $CH_3$). IR (nujol/NaCl) [cm-1]: 3309 (sh, w, amide NH), 3229 (s, str, H bonded amide NH/carboxylic OH), 3166 (s, str, H bonded amide NH/carboxylic OH), 3083 (s, str, H bonded amide NH/carboxylic OH), 1834 (s, str, oxaz C=O), 1809 (s, m, H bonded oxaz C=O), 1743 (s, str, carboxylic CO), 1663 (s, str, oxaz C=N), 1639 (s, br, str, amide CO). Anal. Calcd for $C_{21}H_{32}N_2O_5$. ($C_6H_{12}$)0.25: C, 65.35; H, 8.53; N, 6.77. Found: C, 65.07; H 8.67: N, 6.68%. Presence of solvate cyclohexane was confirmed by $^{13}$C NMR.

Macrocyclization Reactions

Examples of several synthetic routes for the preparation of macrocyclic tetraamido ligands follow.

Phosphorus Trichloride Coupling

Phosphorus trichloride coupling of the amide-containing intermediate (A—L—A) to aromatic 1,2-diamines yields macrocyclic tetraamides safely, cheaply and in high yield. Two distinct variations of the $PCl_3$ coupling method are useful, the differences relate to the order of addition and choice of reagents utilized. These methods are applicable to the preparation of a wide variety of different macrocycles with different electronic substituents present on the bridge diamine, or steric substituents present on the amide intermediate, primarily because of the parallel incorporation of the macro linker type of amide intermediates into all of the syntheses.

EXAMPLE 8

A. Macrocycle Synthesis via $PCl_3$ Coupling

A long neck flask (250 mL) is charged with the amide intermediate of Examples 2–7, (10 mmol) a stir bar and then baked in the oven (80°–100° C., 30–45 mins). The hot flask is placed under $N_2$, aryl diamine (10 mmol) is added and anhydrous pyridine (50 mL, sure seal) cannulated in. The flask is heated (50°–60° C.) and $PCl_3$ (d=1.574 g/mL, 1.72 mL, 20 mmol) syringed in as quickly as possible without excessive refluxing. This is an exothermic reaction, so caution should be used. The temperature is then increased to reflux or just below reflux (100°–115° C.) and the reaction allowed to proceed under $N_2$ (48 h). After the acylation is complete, the contents of the flask are acidified with HCl (1 eq., ca. 60 mL) to a final pH 2. The mixture is transferred to an erlenmeyer (water is used to rinse the flask) and stirred with $CH_2Cl_2$ (300 mL, 2–3 h), then extracted with additional $CH_2Cl_2$ (2×150 mL). The combined organic layers are washed with dilute HCl (0.1M, 2×100 mL) followed by dilute aqueous $Na_2CO_3$ (2×5 g/100 mL). The organic solvents are removed on the rotary evaporator to yield crude product (30%). The weight of crude product is usually equivalent to the initial weight of diamine.

B. Macrocycle Synthesis via $PCl_3$, Coupling

A long neck flask (250 mL) is charged with $MgSO_4$ (5 g), a stir bar, aryl diamine (10 mmol) and pyridine (50 mL, dried over 4 Å mol sieves) then placed under $N_2$ $PCl_3$ (d=1.754 g/mL, 1.72 mL, 20 mmol) is added via syringe and the mixture brought to reflux for 30 mins, an orange/yellow precipitate forms. The mixture is cooled somewhat, an amide intermediate (10 mmol) is added, then the mixture is refluxed under $N_2$ (115° C., 48 h). After the acylation is complete, the contents of the flask are acidified with HCl (1 eq., ca. 60 mL) to a final pH 2. The mixture is transferred to an erlenmeyer and stirred with $CH_2Cl_2$ (2×150 mL). The combined organic layers are washed with dilute HCl (0.1M, 2×100 mL) followed by dilute $Na_2Co_3$ (2×5 g/100 mL) The organic solvents are removed on the rotary evaporator to yield crude product (30%). The weight of crude product is usually equivalent to the initial weight of diamine.

Note: For larger scale macrocyclization reactions, the ring closure times are increased to 4–5 days at reflux, and most of the pyridine present at the end of the reaction is removed via rotary evaporation prior to acidification.

EXAMPLE 9

TMDE-DCB from TMDE Intermediate+DCB Diamine 1,2-Diamino-4,5 dichlorobenzene (1.77 g, 10 mmol) was utilized as the aryl diamine with TMDE amide intermediate (3.3 g, 10 mmol) in the $PCl_3$ method A or B macrocyclization reaction. The crude macrocyclic product (2.7 g) was recrystallized from a minimum amount of hot 95% EtOH by evaporation to yield pure TMDE-DCB (1.5 g, 32%). Characterization: $^1H$ NMR ($CD_2Cl_2$) δ[ppm]:7.65 (s, 1H, ArH), 7.35 (s, 2H, amide NH), 6.45 (s, 2H, amide NH), 1.90 (q, 4H, ethyl $CH_2$), 1.57 (s, 12H, $RCH_3$), 0.85 (t, 6H, ethyl $CH_3$). IR (nujol/NaCl) ν[$cm^-$]: 3454 (trace ROH), 3346 (br, amide NH), 1706&1688&1645 (amide CO). Anal. Calcd. for $C_{21}H_{28}Cl_2N_4O_4$; C, 53.51; H, 5.99; N, 11.89. Found C, 53.58; H, 6.09; N, 11.89.

EXAMPLE 10

TMDE-B from TMDE Intermediate+B Diamine 1,2-Diaminobenzene (i.e, o-phenylene diamine)(1.08 g, 10 mmol) was utilized as the aryl diamine with the TMDE amide intermediate (3.3 g, 10 mmol) in the PCl, method A or B macrocyclization reaction. The crude macrocyclic product (1.5 g) was recrystallized from a minimum amount of hot 95% EtOH by evaporation to yield pure TMDE-B (25% from diamine). Characterization: $^1H$ NMR ($CDCl_3$) δ[ppm]; 7.55 (m, 2H, ArH), 7.48 (s, br, 2H, aryl amide NH), 7.17 (m, 2H, ArH), 6.46 (s, br, 2H, alkyl amide NH), 2.07 (m, br, 4H, ethyl $CH_2$), 1.60 (s, 12H, $RCH_3$), 0.89 (t, 6H, ethyl $CH_3$). IR (nujol/NaCl) [$cm^1$]; 3395&3363 (amide NH), 1702&1680&1652&1635 (amide CO). Anal. Calcd. for $CH_{21}H_{10}N_4O_4·H_2O$: C, 59.98; H, 7.67; N, 13.32. Found: C, 60.18; H, 7.20; N, 13.18.

EXAMPLE 11

TMDE-DMB from TMDE Intermediate+DMB Diamine 1,2-Diamino-4,5-Dimethylbenzene (1.36 g, 10 mmol) was utilized as the aryl diamine with Tetramethyl Diethyl amide intermediate (3.3 g, 10 mmol) in the $PCl_3$ method A or B macrocyclization reaction. The crude macrocyclic product (1.6 g) was recrystallized from a minimum amount of hot 95% EtOH by evaporation to yield pure TMDE-DMB (25% from diamine). Characterization: $^1H$ NMR (DMSO $d^6$) δ[ppm]: 8.00 (s, 2H, amide NH), 7.67 (s, 2H, amide NH), 7.28 (s, 2H, ArH), 2.17 (s, 6H, aryl $CH_3$), 1.99 (q, 4H, ethyl $CH_2$), 1.46 (s, 12H, $RCH_3$), 0.75 (t, 6H, ethyl $CH_3$). Ir (nujol/NaCl) ν[$cm^{-1}$]: 3446 (s, m, trace ROH), 3362 (s, str, amide NH), 3348 (sh, m, amide NH), 3332 (s, str, H amide NH), 1696 (amide CO), 1679 (amide CO), 1651 (amide CO), 1641 (amide CO), 1584 (s, m/w, aryl ring/amide). Anal. Calcd. for $C_{23}H_{34}N_4O_4$: C. 64.16; H, 7.96; N, 13.01, Found: C, 64.09, 64.28; H, 8.04, 7.92; N, 12.86, 13.04.

EXAMPLE 12

TMDE-DMOB from TMDE Amide Intermediate+ DMOB Diamine 1,2-Diamino-4,5-Dimethoxybenzene. 2 HBr (5.0 g, 15 mmol) prepared as above was utilized as the aryl diamine directly with the Tetramethyl Diethyl amide intermediate (5.0 g, 15 mmol) in a 1.5 scale PCl, method A or B macrocyclization reaction. The crude macrocyclic product (3.57 g) was recrystallized from a minimum amount of hot 80–85% EtOH (1 g/40 mL) by evaporation to yield pure TMDE-DMOB (30% from diamine). Characterization: $^1H$ NMR ($CD_2Cl_2$) [ppm]: 7.26 (s, 2H, amide NH), 7.01 (s, 2H, ArH) 6.41 (s, 2H, amide NH), 3.80 (s, 6H, aryl $OCH_3$), 2.07 (q, br, 4H, ethyl $CH_2$), 1.54 (s, 12H, $RCH_3$), 0.90 (t, 6H, ethyl $CH_3$). IR (nujo/NaCl) ν[$cm^{-1}$]: 3451 (s, m, H bonded $H_2O$), 3391&3347 (amide NH), 1695&1670&1655 (amide CO). Anal. Calcd. for $C_{23}H_{34}N_4O_6$, $(H_2O)_{0.33}$: C, 58.96; H, 7.46; N, 11.96, Found (ESU); C, 58.90; H, 7.26; N, 11.76. Presence of solvate $H_2O$ was confirmed by $^1H$ NMR and IR.

EXAMPLE 13

TMDE-Nap from TMDE Intermediate+Nap Diamine 4,5 Diamino Napthalene (1.68 g, 10 mmol) was utilized as the aryl diamine with the Tetramethyl Diethyl amide intermediate (3.3 g, 10 mmol) in the PCl, method A or B macrocyclization reaction. Unoptimized yield was 15–20% from diamine. $^1H$ NMR ($CDCl_3$) δ[ppm]: 8.05 (s, 2H, ArH α ring), 7.75 (m, 2H, ArH β ring), 7.55 (s, 2H, Ar amide NH), 7.35 (m, 2H, ArH β ring), 6.45 (s, 2H, alkyl amide NH), 2.15 (m, br, 4H, ethyl $CH_2$,), 1.65 (s, 12H, $RCH_3$), 0.90 (t, 6H, ethyl $CH_3$).

EXAMPLE 14

HM-DCB from HM Intermediate+DCB Diamine 1,2-Diamino-4,5-Dichlorobenzene (1.77 g, 10 mmol) was utilized as the diamine with Hexa Methyl amide intermediate (3.02 g, 10 mmol) in the $PCl_3$, method A or B macrocyclization reaction. The crude macrocycle (1.33 g, 30%) was recrystallized from a minimum of hot n-propanol by evaporation, 1st crop recrystallization yield was 60%. Characterization: $^1H$ NMR δ[ppm]: 7.69 (s, 2H, ArH), 7.39 (s, 2H, amide NH), 6.44 (s, 2H, amide NH), 1.58 (s, 12H, arm methyls), 1.53 (s, 6H, malonate methyls), small n-propanol peaks were noted. IR (nujol/NaCl) ν[$cm^{-1}$]: 3503 (s, br, m-w, n-propanol OH, 3381 (sh, m, amide NH), 3338 (s, str, amide NH), 1689 (s, str, amide CO), 1643 (s, str, amide CO). Anal. Calcd. for $C_{19}H_{24}N_4O_4Cl_2$. $(C_3H_8O)_{0.2}$: C, 51.70; H, 5.57, N, 12.30%. Found C, 51.69; H, 5.63; N, 12.33.

EXAMPLE 15

HM-DMOB and HM-B from HM Intermediate+ DMOB or B Diamine

The HM intermediate has also been used to synthesize HM-B and HM-DMOB according to the same method and with similar results to those obtained in example 14 for the dichloro derivative. 1H NMR data for HM-DMOB in $CDCl_3$ δ[ppm]: 7.65 (s, 2H, amide NH), 7.21 (s, 2H, aryl CH), 6.72 (s, 2H, amide NH), 4.00 (s, 6H, methoxy $CH_3$), 1.76 (s, 12H, arm methyls), 1.58 (s, 6H, malonate methyls). $^1H$ NMR data for HM-B in $d^5$ pyridine δ[ppm]: 8.55 (s, 2H, amide NH), 8.40 (s, 2H, amide NH), 7.81 (m, 2H, ArH aa'bb'), 7.10 (m, 2H, ArH aa'bb'), 1.77 (s, 12H, arm methyls), 1.73 (s, 6H, malonate methyls). The amide peaks tend to shift a few tenths of a ppm in the presence of impurity species such as water, acids, etc.

EXAMPLE 16

DiCyHexDE-DCB from DiCyHexDE Intermediate+ DCB Diamine 1,2-Diamino-4,5-Dichlorobenzene (1.77 g, 10 mmol) was utilized as the aryl diamine with Di Cy Hex Diethyl amide intermediate (3.3 g, 10 mmol) in the $PCl_3$, method A or B macrocyclization reaction. Due to the increased steric hindrance an increased ring closure reaction time is recommended (3–4 days as opposed to the usual 48 h). Cy Hex Oxazalones formed as a side product during the reaction are not removed by the acid base workup, so it is necessary to triturate/wash the initially isolated $CH_2Cl_2$ soluble product with pentane to remove the oxazalones. Evaporation of the pentane washes allows for recycling of the oxazalones. The crude pentane insoluble product was recrystallized by dissolving in $CH_2Cl_2$ or $CHCl_3$, adding cyclohexane until slightly cloudy and then evaporating in air (1–2 days) to yield the white microcrystalline DiCyHexDE-DCB product, which was collected by filtration (1.38 g, 25% from diamine). Recrystallization from hot neat toluene with evaporation also appears promising. Characterization: $^1H$ NMR ($CDCl_3$) δ[ppm]: 7.70 (s, 2H, ArH), 7.45 (s, 2H, amide NH), 6.45 (s, 2H, amide NH), 2.35 (m, br, 4H, cyhex), 2.00 (m, br, ≈8H, cyhex/ethyl $CH_2$), 1.70 (m, br, ≈8H, cyhex), 1.30 (m, br, ≈4H, cyhex), 0.90 (t, 6H, ethyl $CH_3$). Anal. (Dried at 100° C.) Calcd. for $C_{27}H_{36}Cl_2N4O_4$, $(C_6H_{12})_{0.2}$: C, 59.60; H, 6.81; N, 9.86, Found: C, 59.60; H, 6.77; N, 9.77. Presence of solvent cyclohexane was confirmed by $^1H$ and $^{13}C$ NMR.

EXAMPLE 17

DiCyHexDE-B from DiCyHexDE Intermediate+B Diamine 1,2-Diaminobenzene (ortho-phenylene diamine, 1.08 g, 10 mmol) was utilized as the aryl diamine in a preparation analogous to that for DiCyHexDE-DCB, to yield DiCyHexDE-B (1.25 g, 26% from diamine). Characterization: $^1H$ NMR ($DC_3CN$) δ[ppm]: 7.62 (s, 2H, aryl amide NH), 7.51 (m, 2H, ArH), 7.18 (m, 2H, ArH), 6.71 (s, 2H, alkyl amide NH), 2.12 (m, 6H, Cyhex), 1.85 (q&m, ethyl $CH_2$ & cyhex), 1.62 (m, cyhex), 1.37 (m, cyhex), 0.90 (t, 6H, ethyl $CH_3$), 0.85 (m, cyhex). IR (nujol/NaCl) ν[$cm^{-2}$]: 3750 (s, m, $H_2O$), 3385 (s, str, amide NH), 314 (s, str, amide NH), 3258 (s, m, br, H bonded amide NH), 1694 (s, str, amide CO), 1651 (s, str, amide CO), 1594 (s, m, aryl ring/amide).

EXAMPLE 18

DiCyHex Diethyl Bis Oxazalone

This product was obtained as a byproduct of the $PCl_3$, macrocyclization reaction of DiCyHex Di Ethyl Amide Intermediate with o-phenylene diamine. The bis oxazalone is not removed by the acid base workup (it is a neutral molecule and very organic soluble). Washing of the crude macrocyclic/oxazalone product with pentane extracts most of the bis oxazalone into the pentane. Air evaporation of the pentane layer yields the pure bis oxazalone as large (1 cm×1 cm×0.5 cm) transparent prisms. Due to the bulky hydrophobic CyHex groups this oxazalone is much more resistant to hydrolysis than the corresponding methyl derivative. Characterization of the bis oxazalone: $^1H$ NMR ($CD_3CN$) δ[ppm]: 2.05 (q, 4H, ethyl $CH_2$), 1.8–1.4 (Unresolved Cy Hex Groups), 0.88 (t. t H, ethyl $CH_3$). 13C NMR broadband decoupled ($CD_3CN$) δ[ppm]: 181.0 (oxaz C=O), 162.7 (oxaz C=N) 69.0 (oxaz cyhex quat), 49.0 (malonate quat), 34.3 (cyhex α methylenes), 25.5 (cyhex γ methylenes), 24.9 (malonate methylenes), 21.8 (cyhex β methylenes), 8.3 (ethyl $CH_3$). IR (nujol/NaCl) ν[$cm^{-1}$]: 1822 (s, str, br, oxaz C=O), 1662 (s, str, oxaz C=N). Anal. (Dried at 50° C.) Calcd. for $C_{21}H_{30}N_2O_4$: C, 67.36; H, 8.07; N, 7.48, Found: C, 67.26; H, 8.15; N, 7.64.

Syntheses of Chelate Complexes

EXAMPLE 19

$[Et_4N]2$ and $[Et_4N]3$, [the tetraethylammonium salts of iron(III) chloro TMDE-DCB monoanion and iron(III) aquo TMDE-DCB monoanion respectively].

The parent macrocyclic tetraamide of any of Examples 10–18 above (525 mg, 1.1 mmol) is dissolved in tetrahydrofuran (40 mL, Aldrich) under $N_2$. Using schlenk techniques, tert-butyllithium (2.6 mL, 4.4 mmol, 1.7M in 2,4-dimethylpentane, Aldrich) was added to the solution under $N_2$ at −108° C. Ferrous chloride (anhydrous, 155 mg, 1.2 mmol, Alfa) was then added and the solution warmed to room temperature with stirring (16 h), to yield an olive-green precipitate, an air sensitive $Fe^{II}$ complex. Air was admitted through a drying tube (2 h), and the orange solid was collected and washed with $CH_2Cl_2$ (2×10 mL). The resulting orange powder was dried under reduced pressure. Yield: 595 mg (≈93%). Because of variable salvation and limited solubility, the lithium salt was converted to the tetraethylammonium salt for further use. The lithium salt (595 mg) in $CH_3OH$ (50 mL) was loaded on an ion exchange column (Dowex® 50X2-100, 25 g, 2 cm×12.5 cm) that had been presaturated with $[Et_4N]^+$ cations, and the orange band was eluted with $CH_3OH$ (100 mL). The solvent was removed under reduced pressure. The residue was suspended in $CH_2Cl_2$ (20 mL) and the mixture was filtered. The solvent was removed from the mother liquor under reduced pressure giving an orange hygroscopic glassy residue of $[Et_4N]2$ that was used without further purification. IR (Nujol/NaCl, $cm^{-1}$): 1619 (ν(CO)amide), 1575 (ν(CO) amide), 1534 (ν(CO)amide). Careful purification of an iron (III) starting material was more conveniently approached by dealing with the axial aqua monoanionic complex rather than this axial chloro dianionic complex. $[Et_4N]2$ (550 mg, ca. 0.7 mmol) was dissolved in $CH_3CN$ (50 mL). Silver tetrafluoroborate (140 mg. 0.7 mmol) was dissolved in $CH_3CN$ (2 mL) and was added to the solution which was stirred (1 h). The AgCl precipitate was filtered off and the solvent removed under reduced pressure. The resulting $[Et_4N]3$ was further purified by elution through a silica gel column (8% MeOH in $CH_3Cl_2$). The solvent was removed under reduced pressure and the product was recrystallized from $H_2O$. Yield: 360 mg (≈77% variable salvation with water was found in different microcrystalline samples). IR (Nujo/NaCl, $cm^{-1}$): 1590 (ν(CO)amide), 1565 (ν(CO) amide), 1535 (ν(CO) amide). Anal. Calcd for $C_{29}H_{46}N_5FeO_5Cl_2$. ($H_2O$) : C, 50.52; H, 7.02; N, 10.16.: Cl, 10.28. Found: C, 50.24; H, 6.84; N, 9.82; Cl, 10.32. ESIMS (negative ion): m/z 522.2, $[3-H_2O]^{1-}$ (100%); m/z 269.7, $[3-H^+]^{2-}$ (18%).

EXAMPLE 20

$[Et_4N]4$, [the tetraethylammonium salt of iron(IV) chloro TMDE-DCB monoanion]

$[Et_4N]2$ (500 mg, ca. 0.6 mmol) was dissolved in $CH_2Cl_2$ (30 mL). Ammonium cerium(IV) nitrate (10.3 g, 18.3 mmol) was added to the solution and the mixture was stirred (2 h). The solid cerium salts were removed by filtration. The purple product was obtained by removing the solvent under reduced pressure and drying under vacuum. Yield: 400 mg (≈95%). Purple crystals were obtained by recrystallization from $CH_2Cl_2/Et_2O$. IR (Nujol/NaCl, $cm^{-1}$): 1688 (ν(CO) amide), 1611 (ν(CO) amide), 1582 (ν(CO) amide). ESIMS (negative ion): m/z 557 $[4]^{-1}$ (100%); m/z 522, $[4- Cl]^{1-}$ (65%).

EXAMPLE 21

Synthesis of $[Ph_4P]5$ [the tetraphenylphosphonium salt of iron(IV) cyano TMDE-DCB monoanion] from $[Et_4N]4$ [the tetraethylammonium salt of iron(IV) chloro TMDE-DCB monoanion] and NaCN.

$[Et_4N]4$ [the tetraethylammonium salt of iron(IV) chloro TMDE-DCB monoanion] (225 mg, 0.33 mmol) was suspended in $H_2O$ (10 mL). Sodium cyanide (140 mg, 2.85 mmol) was dissolved in $H_2O$ (10 mL) and added to the suspension and the mixture was sonicated (Branson 1200, 0.5 h). The purple suspension changed to a deep blue solution and nearly all the solid material dissolved. The mixture was filtered and the blue product was precipitated by adding $PPh_4Cl$ [tetraphenylphosphonium chloride] dissolved in water (600 mg, 1.6 mmol, 10 mL, Aldrich). The blue precipitate was collected and washed with $H_2O$ (2×10 mL). Yield: 250 mg (0.28 mmole, ≈85%). This material (120 mg) was further purified by thin layer chromatography (TLC) (Silica gel plate, GF, 20 cm×20 cm×1000 μm, 10:1 $CH_2Cl_2:CH_3CN$). The blue material was extracted from the silica gel with $CH_3CN:CH_2Cl_2$ (1:1, 60 mL). The solvent was removed under reduced pressure and the residue was dissolved in $CH_2Cl_2$(3 mL) and filtered. Addition of pentane (150 mL) gave a blue powder (90 mg, 0.10 mmol) Yield on purification: (75%). IR (Nujol/NaCl, $cm^{-1}$): 2129 (ν(CN)), 1659 (ν(CO) amide), 1598 (ν(CO) amide), 1571 (ν(CO) amide). Anal. Calcd for: $C_{46}H_{44}N_5FeOCl_2P$: C, 62.18; H, 4.99; N, 7.88; Cl, 7.98. Found: C, 61.96; H, 5.04; N, 7.84; Cl, 8.06. ESIMS (negative ion): m/z 548.2, $[5]^{1-}$ (100%); m/z 522.1, $[5-CN]^{1-}$ (20%). For $^{13}C$-labeled cyanide: m/z 549.2, $[5]^{1-}$ (100%); m/z 522.1, $[5-\,^{13}CN]^{1\,-}$ (8%).

EXAMPLE 22

The Synthesis of $[Ph_4P]5$ [the tetraphenylphosphonium salt of iron(IV) cyano TMDE-DCB monoanion] from Nitrile Cyanide Sources.

$[Ph_4P]5$ [the tetraphenylphosphonium salt of iron(IV) cyano TMDE-DCB monoanion] can be formed in the presence or absence of base. In the absence of base, the blue color fades to yellow-orange as the solvent is removed in the workup procedures. Therefore, product isolation to obtain the blue solid is best carried out in the presence of added base at a pH range of 9–10. The following reaction yields $[PH_4P]5$ with each of $CH_3CN$, $CD_3CN$, $CH_3CH_2CN$ and $(CH_3)_2CHCN$ as the solvent substrates. Base was not added to the catalytic reactions described. It was determined that the blue compound is an effective catalyst precursor by adding isolated $[Ph_4P]5$ to an acetonitrile solution of TBHP (tertiary butyl hydroperoxide), both the solvent and oxidant were consumed indicating that although $[Ph_4P]5$ is formed as an end product of the catalytic oxidation process it is not a deactivated form of the catalyst.

EXAMPLE 23

The Synthesis of $[Ph_4P]5$ in the Presence of Base $[Et_4N]3$ (160 mg, 0.23 mmol) was dissolved in the chosen nitrile solvent (6 mL), see Example 19. Tetraethylammonium hydroxide base was added (20 wt, 0.370 mL, 0.52 mmol, Aldrich), then t-butyl hydroperoxide (90%, 0.605 mL, 5.4 mmol, Aldrich) was added dropwise with stirring (20 min) resulting in a blue solution. The remaining nitrile was removed under reduced pressure, leaving an oily blue residue which was dissolved in $H_2O$ (15 mL) and filtered. The blue material was precipitated from the filtrate by addition of an aqueous solution of $PPh_4Cl$ (800 mg, 2.1 mmol, Aldrich, 10 mL). The blue precipitate was collected and washed with $H_2O$ (2×10 mL). Yield: 130, 0.15 mmol (65%). Further purification was carried out as described in the $[Ph_4P]5$ section, Example 25.

EXAMPLE 24

X-ray Crystal Structure Data and Refinement for $[Et_4N]3$ $H_2O$ $C_{29}H_{48}Cl_2FeN_5O_6$, M=689.47, Triclinic, Space group P-1, a=9.899(2); b=11.771(2); c=14.991(4) Å, =95.33(2);β=100.09(2); γ=92.31(2)°, V=1709.6(6) Å$^3$, $D_{obs}$=1.33 g cm$^{-3}$, $D_{calcd}$(Z=2)=1.339 g cm$^{-3}$, T=293 K, λ=0.71069 Å, μ=0.64 mm$^{-1}$, trans coeff. 0.87–1.00. Diffraction data were collected at room temperature on an Enraff-Nonius CAD-4 diffractometer using graphite monochromated Mo-K$\overline{\alpha}$ radiation. Three reflections were monitored throughout data collection, only random fluctuations in intensity being observed. The structure was solved by direct methods. Hydrogen atoms bonded to the carbon were included in calculated positions with C/H bond distance of 0.96 Å and were refined using a riding model with a thermal parameter 20% greater than the parent carbon. Hydrogen atoms of the water molecule were located from electron density difference maps and their coordinates allowed to refine with the thermal parameter fixed at 20% greater than that of the oxygen. Refinement was by full-matrix least squares on F$^2$ with scattering factors taken from the International Tables. All non-hydrogen atoms were refined with anisotropic thermal parameters. The final difference maps were featureless. Refinement converged to R=0.053, wR2=0.112 with weights $1.0/[\sigma^2 F_o^2) + \{0.0652 \ (F_o^2 + 2F_c^2)/3\}^2]$ for 2262 observed reflections.

EXAMPLE 25

X-ray Crystal Structure Data and Refinement for [Et$_4$N]4

Single crystals of [Et$_4$N]4. at 20±1° C. are monoclinic, space group P2$_1$/c-C$^5_{2h}$ (No. 14) with a=9.958(2) Å, b=14.956(3) Å, c=22.688(5) Å, α=90.00, β=93.83(2), γ=90.00, V=3372(1) Å$^3$, and Z=4 ($d_{calcd}$=1.357 g cm$^{-3}$; $\mu_a$(CuK$\overline{\alpha}$)=6.17 mm$^{-1}$). A total of 4626 independent absorption-corrected reflections having 2θ (CuK$\overline{\alpha}$)<115.0° were collected using θ-2θ scans and Ni-filtered CuK$\overline{\alpha}$ radiation. The structure was solved using "Direct Methods" techniques with the NICOLET SHELXTL software package as modified at Crystalytics Company. The resulting structural parameters have been confined to a convergence of R$_1$ (unweighted, based on F)=0.037 for 2680 independent reflections having 2θ (CuK$\overline{\alpha}$)<115.0° and I>3σ(I). The ten methyl groups were refined as rigid motors with sp$^3$-hybridized geometry and a C—H bond length of 0.96 Å. The initial orientation of each methyl group was determined from difference Fourier positions for the hydrogen atoms. The final orientation of each methyl group was determined by three rotational parameters. The refined positions for the rigid rotor methyl groups have C—C—H angles which ranged from 103°–118°. The remaining hydrogen atoms were included in the structure factor calculations as idealized atoms (assuming sp$^2$- or sp$^3$-hybridization of the carbon atoms and a C—H bond length of 0.96 Å) riding on their respective carbon atoms. The isotropic thermal parameter of each hydrogen atom was fixed at 1.2 times the equivalent isotropic thermal parameter of the carbon to which it is covalently bonded.

EXAMPLE 26

Lignin Bleaching With Hydrogen Peroxide and Fe-DCB at pH 10

Into a 1 cm pathlength quartz cuvette containing 3.0 mL of 0.1M NaHCO$_3$/Na$_2$CO$_3$ (pH 10) thermostatted at 25° C. was added 60 μL of a saturated alkali lignin solution and 300 μL of catalyst stock solution (1.24×10$^{-4}$M Fe-DCB (wherein R' and R" are methyl), all in water. The solution was stirred and 3.8 μL of 30% H$_2$O$_2$ was added. Absorbance changes at 350, 376, 400, 426, 450, and 476 nm were measured using a Hewlett-Packard UV/Vis spectrophotometer operating in the single cell Kinetics mode. Upon addition of the H$_2$O$_2$, the absorbance increased rapidly at all wavelengths and then decreased rapidly. After 15 min the absorbance at each wavelength was below the starting value indicating that lignin bleaching had occurred. A second addition of 60 μL of lignin was added which caused the absorbances to rise rapidly like before and then following the initial rise decrease more slowly than before. Bubbles formed throughout the experiment.

After 30 mins., an additional 3.8 μL of H$_2$O$_2$ was added. The behavior was similar to that observed previously. A rapid increase in absorbance followed by a decay.

EXAMPLE 27

Lignin Bleaching Without Fe-DCB at pH 10

The steps of Example 26 were repeated with the exclusion of the catalyst. Into a 1 cm pathlength quartz cuvette containing 3.0 mL of 0.1M NaHCO$_3$/Na$_2$CO$_3$ (pH 10) thermostatted at 25° C. was added 60 μL of a saturated alkali lignin solution and the mixture stirred. A short period after data acquisition was initiated, 3.8 μL of 30% H$_2$O$_2$ was added.

The absorbance measurements were taken using the same parameters as in Example 26.

Upon addition of the H$_2$O$_2$, all six wavelengths showed a rise in absorbance. The rise was not rapid and did not spike as in the catalyzed reaction. The absorbance gradually began to slope downwards, but did so very slowly. No bubbles were observed in the mixture within the first 15 min. By the end of the hour, bubbles began to appear.

Comparison of the preliminary experiments in Examples 26 and 27 indicate that the addition of the activator of the present invention increases the rate at which H$_2$O$_2$ bleaches lignin.

EXAMPLE 28

Lignin Bleaching With Hydrogen Peroxide, A Sequesterant and No Fe-DCB at pH 10

The steps of Example 27 were repeated with the addition of a sequesterant, DEQUEST 2066, 2 μL, a chelating agent for free metal ions. The addition of H$_2$O$_2$ gave a gradual rise and decay pattern similar to that seen in Example 27.

EXAMPLE 29

Lignin Bleaching With Hydrogen Peroxide, A Sequesterant and no Fe-DCB at pH 7

The steps of Example 27 were repeated at pH 7 using a 0.0087 molal KH$_2$PO$_4$/0.030 molal Na$_2$HPO$_4$ buffer. 2 μL DEQUEST 2066 chelating agent was added to the cuvette. No discernible bleaching occurred within the 1 hr timeframe of the experiment. Minimal activity was observed in the 350 nm absorbance trace, but was attributed to noise.

EXAMPLE 30

Lignin Bleaching With Hydrogen Peroxide, FE-DCB and A Sequesterant at pH 10

Into a cuvette equipped with a stir bar, 1 equivalent of the catalyst of Example 26 (300 μL stock solution of Fe-DCB), 60 μL saturated lignin solution buffered as before and 2 μL DEQUEST chelating agent were mixed. Absorbance was measured using the same parameters as described in Examples 26 and 27.

After 1–2 min., 1000 equivalents 30% $H_2O_2$ (3.8 μL) was added to the cuvette. This caused the rapid rise in absorbance followed by rapid decrease as described in Example 26.

After 20 min., an additional 60 μL lignin was added to the cuvette. The absorbance at all wavelengths rose more slowly and then decayed more slowly than following the addition of the $H_2O_2$.

After 30 min., an additional equivalent (300 μL) of catalyst (Fe-DCB) was added. No significant changes were observed.

After 40 min., an additional 3.8 μL $H_2O_2$ was added to the cuvette. This caused a significant decrease in the absorbance at all wavelengths indicating that lignin bleaching was again occurring.

EXAMPLE 31

Lignin Bleaching With Hydrogen Peroxide, Fe-DCB, and A Sequesterant at pH 7 absorbance should be changed to absorbance.

Example 29 was repeated but with the addition of 300 μL catalyst. 3.8 μL 30% $H_2O_2$ was added after a few cycles. Upon the addition of $H_2O_2$, the absorbances rose at each of the six wavelengths used in Example 26, but not dramatically. The absorbances continued to rise slowly for the first 15 min., plateaued, and then began to fall for all six wavelengths. After one hour, the absorbances were higher than the initial absorbance.

EXAMPLE 32

Sustained Catalyst Activity

Into a 1 cm pathlength quartz cuvette containing 3.0 mL if 0.1M $NaHCO_3/Na_2CO_3$ (pH 10) thermostatted at 25° C. was added 60 μL of a saturated alkali lignin solution, 300 μL (12.4 μM) of catalyst stock solution (1.24×10$^{-4}$M Fe-DCB), and 2 μL Dequest 2066 all in water. The mixture was stirred, data acquisition was initiated as in Example 26, and then 19 μL (5000 equivalents) of 30% $H_2O_2$ was added. After the first rapid rise in absorbance followed by rapid decay, aliquots of 60 μL saturated alkali lignin solution and 19 μL (5000 equivalents) of 30% $H_2O_2$ were added every 15 min.

The results obtained at the 476 nm monitored wavelength are shown by the solid line in the graph of FIG. 1. Similar results were obtained at the other wavelengths monitored. Additions of lignin and $H_2O_2$ are shown by asterisks.

For comparison, a cuvette of the saturated solution of lignin, chelating agent and $H_2O_2$ without catalyst was prepared and the absorbance measured. The results are shown by the dashed line in FIG. 1.

EXAMPLE 33

Sustained Catalyst Stability

Figure 5:
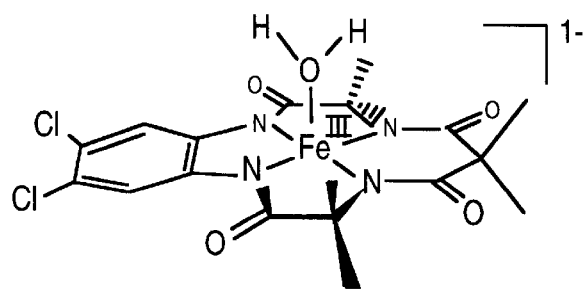
FIG. 5 is a graph comparing the sustained catalyst stability of preferred embodiments of the invention versus control.
Figure 5:
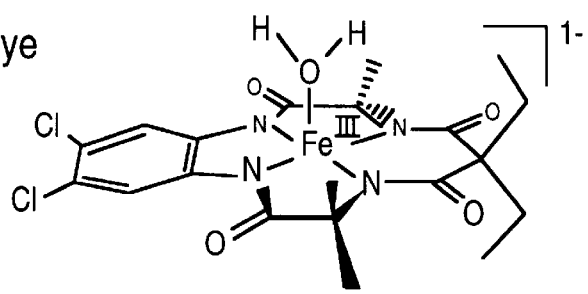
Figure 5:
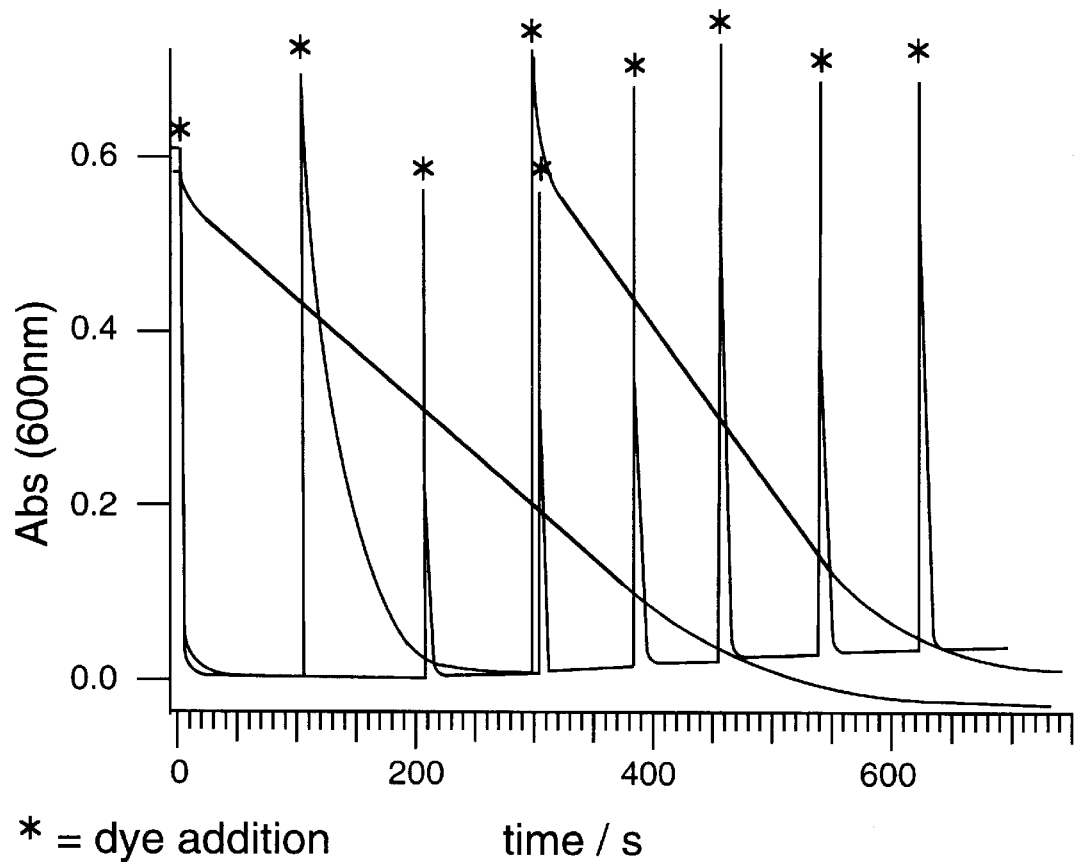

With reference to FIG. 5, the catalytic longevity of two embodiments of the invention were compared. Compound 1 had substitutents R' and R" each as $CH_3$, while Compound 2 had substitutes R' and R" each as —$CH_2CH_3$. The control was no catalyst added.

The conditions were pH 9, room temperature (21.1° C.), with a buffer system of $NaHCO_3/Na_2CO_3$. Oxidant was 4 mM (30%) $H_2O_2$. At each of the asterisks, 12 μM pinacyanol chloride dye was added.

As can be seen from the graph in FIG. 5, each addition of dye where Compound 1 was present resulted in almost immediate decolorization. Compound 2, the diethyl compound, had more gradual decolorization. The control showed only a very gradual rate of decolorization.

From the foregoing, it can be seen that the inventive compounds, and especially Compound 1, are effective in oxidizing and decolorizing extraneous or free flowing dyes released from colored fabrics which are washed in a wash liquor. Thus, the inventive macrocyclic tetraamido compounds provide a unique benefit to an oxidant system, namely dye scavenging, thus preventing the transfer of extraneous and thus, unwanted dyes from one fabric to another in the wash liquor.

Examples 34–38 are further examples of the unique dye transfer inhibition properties of the inventive macrocyclic tetraamido ligands. In Examples 34–35, spectra and absorbance-time curves were recorded on a Shimadzu spectrophotometer. The samples were scanned over the wavelength (λ) range 350 to 700 nm prior to the addition of peroxide or catalyst to determine wavelength for the dye's maximum absorbance. The spectrophotometer was then set to peak wavelength and the peroxide and/or catalyst were added. Changes in the peak absorbance after 2 minutes were reported.

Acid Blue 25 was monitored at 600 nm. The samples were performed at 25° C. in a 1 cm cuvette containing 2 ml solution.

EXAMPLE 34

Bleaching of Acid Blue 25 in Solution

To a solution of Acid Blue 25 [120 mg/l (dye content 45%), initial absorbance at 600 nm was 1.2] was added: (a) 20 ppm A.O. $H_2O_2$; (b) 20 ppm A.O. $H_2O_2$+1 ppm of the inventive compound wherein Z and Y are each hydrogen (hereafter "FeB"); and (c) 20 ppm A.O. $H_2O_2$+1 ppm of the inventive compound wherein Z and Y are each chloro (hereafter "FeDCB"). As shown below, only systems containing catalysts gave any bleaching effect of the dye (monitored as observed change in absorbance at 600 nm in two minutes). As a further comparison, the absorbance loss caused by sodium hypochlorite (5.25% solution, added at 20 ppm $Av.Cl_2$). The results are tabulated below:

| Bleaching System | Absorbance Loss after 2 min. |
| --- | --- |
| 26 ppm $H_2O_2$ | 0 |
| 20 ppm $H_2O_2$ + ppm FeB | 1.15 |
| 20 ppm $H_2O_2$ + ppm FeDCB | 1.15 |
| 20 ppm Av. $Cl_2$ NaOCl | 0 |

A large absorbance loss means more dye has been decolorized. The foregoing data demonstrates that when the inventive catalysts are used, there is efficient dye transfer inhibition. As compared with the amount of dye added (1.2 initial absorbance), the loss of dye is greater than 90% (1.15÷1.2×100%=95.83%).

EXAMPLE 35

Bleaching of Acid Orange 8 in Solution

Experiments were performed as in Example 34, above, except that a solution of Acid Orange 8 (210 mg/l, dye content 65%), initial absorbance at 490 nm was 1.2). Bleaching was measured as change in absorbance at 490 nm.

| Bleaching System | Absorbance Loss after 2 min. |
| --- | --- |
| 20 ppm $H_2O_2$ | 0 |
| 20 ppm $H_2O_2$ + 1 ppm FeB | 1.15 |
| 20 ppm $H_2O_2$ + 1 ppm FeDCB | 1.15 |
| 20 ppm Av. $Cl_2$ NaOCl | 0.17 |

Once again, as compared with the amount of dye added 1.2 initial absorbance), the loss of dye is greater than 90% (1.151.2×100%=95.83%). As compared with the amount of dye added (1.2 initial absorbance), the loss of dye is greater than 90% (1.151.2×100%=95.83%). The dye transfer (ΔE) was calculated again, in accordance with the procedures set forth in the co-pending application Ser. No. 08/396,853, filed Mar. 1, 1995, of Johnson et al., entitled "LAUNDRY ARTICLE FOR PREVENTING DYE CARRY-OVER AND INDICATOR THEREFOR." ΔE averages the reflectance changes of an item of fabric prior to and after washing according to the equation set forth therein. An increase in the calculated value of ΔE for a target fabric washed in the presence of a dye source as compared to a target fabric prior to washing indicates that the target fabric has absorbed the dye. All dyes are from Aldrich Chemicals.

In Examples 36 and 37 below, the following conditions were used: 0.95 g of Ultra Tide® laundry detergent (Procter & Gamble) was added to a Terg-O-Tometer bucket with 1.5 liter of warm water, and two 8×8 inch cotton target fabric (large swatch), and, a fabric that released dye to solution. The purpose of the target fabric was to serve as a dye receptor for any extraneous dye which was not decolorized or oxidized. Samples were agitated for 12 minutes after the addition of the dye scavenging system ($H_2O_2$ and catalyst) using a Terg-O-Tometer followed by a two minute ambient temperature water rinse, and 20 minutes of drying in an automatic dryer.

EXAMPLE 36

Dye transfer from Textile to Textile Using Direct Red 79

In order to demonstrate that the effects seen in the above solution experiments (Examples 34–35) were reflected on textiles present in such solutions, experiments were carried out in which clean cotton swatches were immersed in a model wash liquor containing a fabric that released 0.1 g. of Direct Red 79 dye to solution. The amount of dye absorbed by the target fabric was determined by calculated ΔE. The dye transfer inhibition performance was compared against polyvinyl pyrrolidone (PVP), a standard dye transfer inhibitor. In the data then, smaller scores are better.

| Dye Scavenging System | Delta E Signal |
| --- | --- |
| none | 8.6 |
| 18 ppm $H_2O_2$ | 10.5 |
| 21 ppm PVP | 4.2 |
| 18 ppm $H_2O_2$ + 1 ppm FeB | 2.4 |
| 18 ppm $H_2O_2$ + 1 ppm FeDCB | 2 |

The foregoing data demonstrate that not only do the inventive macrocyclic tetraamido compounds possess superior dye transfer inhibitory performance, but are measurably better than polyvinyl pyrrolidone, a known and effective DTI compound.

EXAMPLE 37

Dye transfer from Textile to Textile Using Acid Red 151

Experiments were performed according to Example 36 only using a release fabric that released 0.1 g of Acid Red 151.

| Dye Scavenging System | Delta E Signal |
| --- | --- |
| none | 26.3 |
| 18 ppm $H_2O_2$ | 32.6 |
| 21 ppm PVP | 30.7 |
| 18 ppm $H_2O_2$ + 1 ppm FeB | 2.5 |
| 18 ppm $H_2O_2$ + 1 ppm FeDCP | 2.8 |

In the next example, the performance of FeDCB on mustard and a naturally occurring clay soil were compared against a system containing $H_2O_2$ only. The performance on mustard, which is a cationically charged stain, demonstrates the stain specific superior performance of the inventive compounds.

EXAMPLE 38

Stain Removal of Mustard and Soil

This example demonstrates stain removal under simulated household laundry wash conditions. Fabrics stained with mustard or naturally occurring clay soil were washed with 2 g of All® liquid laundry detergent and an oxidant system (either $H_2O_2$ or $H_2O_2$ and the inventive catalyst FeDCB). Wash conditions were medium water level in warm water, cold water rinse, using a Terg-O-Tometer. Stain removal was measured and calculated using % soil removal (%SRE). Thus, higher scores are preferred.

| Oxidant System | Mustard | Clay Soil |
| --- | --- | --- |
| 18 ppm $H_2O_2$ | 63.6 | 56.3 |
| 18 ppm $H_2O_2$ + 0.5 ppm FeDCB | 71.5 | 59.8 |

In the next example, the anti-redeposition performance of the inventive compounds was compared against a control (no activator compound) and a commercially available organic bleach activator, tetraacetylethylenediamine (TAED).

EXAMPLE 39

Anti-Redeposition Comparison Study

| System | Redeposition |
| --- | --- |
| Control | 0 |
| Control & FeDCB | 1.3 |
| Control & TAED | 0.7 |

The redeposition of soil is a measurement of the fabric using the Stensby Whiteness Calculation following the washing process. This study indicates that stray dyes are being destroyed in the aqueous wash liquor, preventing redeposition on fabrics; and that the invention's performance is superior versus TAED, a commercially available activator.

We claim:

1. A method of bleaching comprising contacting cellulose-based materials with a bleaching composition comprising:

(a) an oxidatively stable activator having the structure

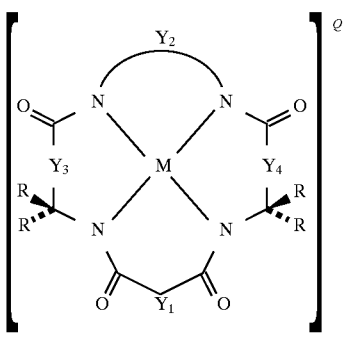

wherein $Y_1$, $Y_3$ and $Y_4$ each represent a bridging group having zero, one, two or three carbon containing nodes for substitution, and $Y_2$ is a bridging group having at least one carbon containing node for substitution, each said node containing a C(R), C($R_1$) ($R_2$), or a C(R)$_2$ unit and each R substituent is the same or different from the remaining R substituents and (i) is selected from the group consisting of alkyl, alkenyl, cycloalkyl, cycloalkenyl, aryl, alkynyl, alkylaryl, halogen, alkoxy, phenoxy, CH$_2$CF$_3$, CF$_3$ and combinations thereof, or (ii) form a substituted or unsubstituted benzene ring of which two carbon atoms in the ring form nodes in the Y unit, or (iii) together with a paired R substituent bound to the same carbon atom form a cycloalkyl or cycloalkenyl ring, which may include at least one atom other than carbon; M is a transition metal with oxidation states of I, II, III, IV, V, VI, VII or VIII or selected from Groups 3, 4, 5, 6, 7, 8, 9, 10 and 11 of the Periodic Table of the Elements; and Q is any counterion which would balance the charge of the compound on a stoichiometric basis; and (b) an amount of a source of an oxidant effective for bleaching said cellulose-base materials.

2. The method of claim 1 further comprising at least one ligand L bound to the metal M.

3. The method recited in claim 1 wherein the oxidant is selected from the group consisting of elemental chlorine, chlorine oxide, chlorineoxoanion, chlorine dioxide, hypochlorite and acidic species thereof.

4. The method of claim 1 wherein the oxidant is selected from the group consisting of elemental halogen, halogen oxide, halogenoxoanion, a peroxy compound, oxygen, air, oxygen in the presence of an adjunct, and combinations thereof.

5. The method recited in claim 4 wherein the adjunct is quinone or anthraquinone.

6. The method recited in claim 1 wherein the oxidant is a peroxy compound.

7. The method recited in claim 6 wherein the peroxy compound is hydrogen peroxide.

8. The method recited in claim 6 wherein the temperature is within the range of ambient to about 80° C.

9. The method recited in claim 6 wherein the temperature is within the range of ambient to about 40° C.

10. The method recited in claim 6 wherein the pH is within the range of 7 and 12.

11. The method of bleaching recited in claim 1 wherein the activator is a macrocyclic tetraamido ligand having the structure:

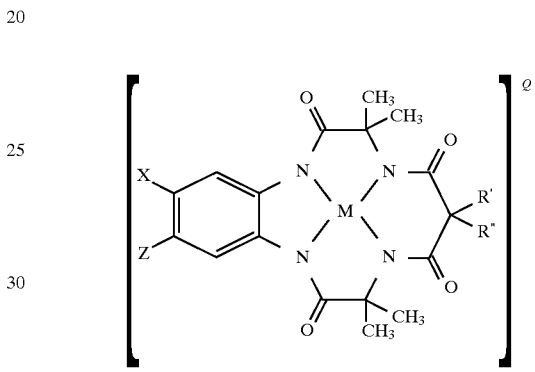

wherein X and Z may be H, electron donating or electron withdrawing groups and R' and R" may be any combination of alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon.

12. The method recited in claim 11 wherein the cellulose-based material is wood pulp.

13. The method recited in claim 11 wherein the oxidant is selected from the group consisting of elemental chlorine, chlorine oxide, chlorineoxoanion, chlorine dioxide, hypochlorite and acidic species thereof.

14. The method of claim 11 further comprising at least one ligand L bound to the metal M.

15. The method of claim 11 wherein the oxidant is selected from the group consisting of elemental halogen, halogen oxide, halogenoxoanion, a peroxy compound, oxygen, air, oxygen in the presence of an adjunct, and combinations thereof.

16. The method recited in claim 15 wherein the adjunct is quinone or anthraquinone.

17. The method recited in claim 15 wherein the peroxy compound is hydrogen peroxide.

18. A method of oxidizing lignin comprising contacting lignin in solution with a bleaching composition comprising:

(a) an oxidatively stable activator having the structure

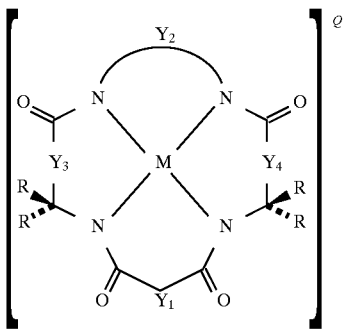

wherein $Y_1$, $Y_3$ and $Y_4$ each represent a bridging group having zero, one, two or three carbon containing nodes for substitution, and $Y_2$ is a bridging group having at least one carbon containing node for substitution, each said node containing a C(R), C($R_1$)($R_2$), or a C(R)$_2$ unit and each R substituent is the same or different from the remaining R substituents and (i) is selected from the group consisting of alkyl, alkenyl, cycloalkyl, cycloalkenyl, aryl, alkynyl, alkylaryl, halogen, alkoxy, phenoxy, $CH_2CF_3$, $CF_3$ and combinations thereof, or (ii) form a substituted or unsubstituted benzene ring of which two carbon atoms in the ring form nodes in the Y unit, or (iii) together with a paired R substituent bound to the same carbon atom form a cycloalkyl or cycloalkenyl ring, which may include at least one atom other than carbon; M is a transition metal with oxidation states of I, II, III, IV, V, VI, VII or VIII or selected from Groups 3, 4, 5, 6, 7, 8, 9, 10 and 11 of the Periodic Table of the Elements; and Q is any counterion which would balance the charge of the compound on a stoichiometric basis; and (b) an amount of a source of an oxidant effective for oxidizing lignin.

19. The method of claim 18 further comprising at least one ligand L bound to the metal M.

20. The method recited in claim 18 wherein the temperature is within the range of ambient to about 80° C.

21. The method recited in claim 18 wherein the temperature is within the range of ambient to about 40° C.

22. The method recited in claim 18 wherein the pH is within the range of 7 and 12.

23. The method recited in claim 18 wherein the oxidant is selected from the group consisting of elemental chlorine, chlorine oxide, chlorine oxoanion, chlorine dioxide, hypochlorite and acidic species thereof.

24. The method of oxidizing lignin recited in claim 18 wherein the activator has the structure:

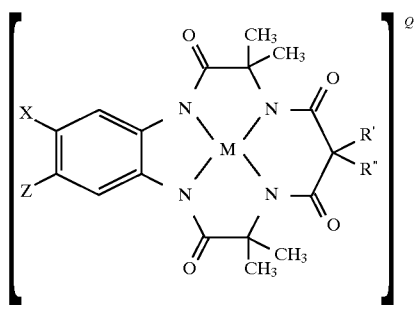

wherein X and Z may be H, electron donating or electron withdrawing groups and R' and R" may be any combination of alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon.

25. The bleaching composition of claim 24 further comprising at least one ligand L bound to the metal M.

26. The method of claim 18 wherein the oxidant is selected from the group consisting of halogen, halogen oxide, halogenoxoanion, elemental halogen, a peroxy compound, oxygen, air, oxygen in the presence of an adjunct, and combinations thereof.

27. The method recited in claim 26, wherein the adjunct is quinone or anthraquinone.

28. The method recited in claim 26 wherein the peroxy compound is hydrogen peroxide.

29. A method of bleaching lignin comprising contacting lignin with a bleaching composition comprising:

(a) an oxidatively stable activator having the structure

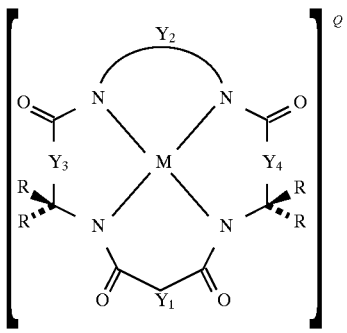

wherein $Y_1$, $Y_3$ and $Y_4$ each represent a bridging group having zero, one, two or three carbon containing nodes for substitution, and $Y_2$ is a bridging group having at least one carbon containing node for substitution, each said node containing a C(R), C($R_1$)($R_2$), or a C(R)$_2$ unit and each R substituent is the same or different from the remaining R substituents and (i) is selected from the group consisting of alkyl, alkenyl, cycloalkyl, cycloalkenyl, aryl, alkynyl, alkylaryl, halogen, alkoxy, phenoxy, $CH_2CF_3$, $CF_3$ and combinations thereof, or (ii) form a substituted or unsubstituted benzene ring of which two carbon atoms in the ring form nodes in the Y unit, or (iii) together with a paired R substituent bound to the same carbon atom form a cycloalkyl or cycloalkenyl ring, which may include at least one atom other than carbon; M is a transition metal with oxidation states of I, II, III, IV, V, VI, VII or VIII or selected from Groups 3, 4, 5, 6, 7, 8, 9, 10 and 11 of the Periodic Table of the Elements; and Q is any counterion which would balance the charge of the compound on a stoichiometric basis; and (b) an amount of a source of an oxidant effective for bleaching lignin.

30. The bleaching composition of claim 29 further comprising at least one ligand L bound to the metal M.

31. The method recited in claim 29 wherein the temperature is within the range of ambient to about 80° C.

32. The method recited in 29 claim wherein the temperature is within the range of ambient to about 40° C.

33. The method recited in claim 29 wherein the pH is within the range of 7 and 12.

34. The method recited in claim 29 wherein the oxidant is selected from the group consisting of elemental chlorine, chlorine oxide, chlorine oxoanion, chlorine dioxide, hypochlorite and acidic species thereof.

35. The method of bleaching lignin recited in claim 29 wherein the activator has the structure:

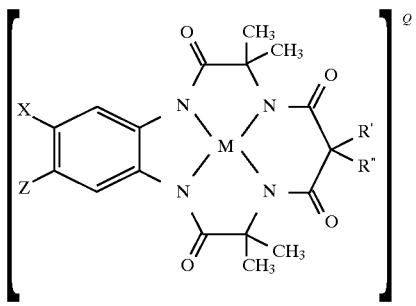

wherein X and Z may be H, electron donating or electron withdrawing groups and R' and R" may be any combination of alkyl, cycloalkyl, cycloalkenyl, alkenyl, aryl, alkynyl, alkylaryl, halogen, alkoxy, or phenoxy substituents, or combine to form a cycloalkyl or cycloalkenyl ring, which may contain at least one atom that is not carbon.

36. The bleaching composition of claim 35 further comprising at least one ligand L bound to the metal M.

37. The method of claim 29 wherein the oxidant is selected from the group consisting of elemental halogen, halogen oxide, halogenoxoanion, a peroxy compound, oxygen, air, oxygen in the presence of an adjunct, and combinations thereof.

38. The method recited in claim 37 wherein the adjunct is quinone or anthraquinone.

39. The method recited in claim 37 wherein the peroxy compound is hydrogen peroxide.

* * * * *

UNITED STATES PATENT AND TRADEMARK OFFICE
CERTIFICATE OF CORRECTION

PATENT NO. : 5,853,428  
DATED : December 29, 1998  
INVENTOR(S) : Collins et al.

It is certified that error appears in the above-identified patent and that said Letters Patent is hereby corrected as shown below:

Figure,  
At the bottom of page 1, delete "0.4mM [Fe(H$_2$O)DCB*]$^-$" and substitute therefor -- 0.4 µM [Fe(H$_2$O)DCB*]$^-$ --;  
Delete "0.4mM [Fe(H$_2$O)DCB]$^-$" and substitute therefor -- 0.4 µM [Fe(H$_2$O)DCB]$^-$ --;  
After "0.0" delete "mM";

Drawings,  
Figure 5,  
Delete "0.4mM [Fe(H$_2$O)DCB*]$^-$" and substitute therefor -- 0.4 µM [Fe(H$_2$O)DCB*]$^-$ --;  
Delete "0.4mM [Fe(H$_2$O)DCB]$^-$" and substitute therefor -- 0.4 µM [Fe(H$_2$O)DCB]$^-$ --;  
After "0.0" delete "mM";

Column 2,  
Line 54, delete "nitrites" and substitute therefor -- nitriles --;

Column 11,  
Line 50, delete "C$_2$-C$_{18}$" and substitute therfor -- C$_{12}$-C$_{18}$ --;

Column 13,  
Line 63, delete "nitrites" and substitute therefor -- nitriles --;

Column 20,  
Line 8, delete "υ[cm$^-$]" and substitute therefor -- υ [cm$^{-1}$] --;

Column 21,  
Line 47, delete "1H" and substitute therefor -- $^1$H --; and

Column 29,  
Line 10, delete "1.2" and substitute therefor -- (1.2 --.

Signed and Sealed this

Fourth Day of December, 2001

Attest:

NICHOLAS P. GODICI  
Attesting Officer    Acting Director of the United States Patent and Trademark Office